(12) United States Patent
Itkowitz et al.

(10) Patent No.: US 12,357,400 B2
(45) Date of Patent: Jul. 15, 2025

(54) SYNTHETIC REPRESENTATION OF A SURGICAL ROBOT

(71) Applicant: INTUITIVE SURGICAL OPERATIONS, INC., Sunnyvale, CA (US)

(72) Inventors: Brandon D. Itkowitz, San Jose, CA (US); Simon P. DiMaio, San Carlos, CA (US); Daniel J. Halabe, Los Altos, CA (US); Christopher J. Hasser, Los Altos, CA (US); Brian D. Hoffman, Mountain View, CA (US); David Q. Larkin, Menlo Park, CA (US); Catherine J. Mohr, Mountain View, CA (US); Paul W. Mohr, Mountain View, CA (US); Tao Zhao, Sunnyvale, CA (US); Wenyi Zhao, Weston, FL (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 59 days.

(21) Appl. No.: 18/187,612

(22) Filed: Mar. 21, 2023

(65) Prior Publication Data
US 2023/0249354 A1    Aug. 10, 2023

Related U.S. Application Data

(60) Continuation of application No. 16/932,373, filed on Jul. 17, 2020, now Pat. No. 11,638,999, which is a
(Continued)

(51) Int. Cl.
*A61B 34/00* (2016.01)
*A61B 34/20* (2016.01)
(Continued)

(52) U.S. Cl.
CPC .............. *A61B 34/25* (2016.02); *A61B 34/30* (2016.02); *A61B 34/37* (2016.02); *A61B 90/36* (2016.02);
(Continued)

(58) Field of Classification Search
CPC ......... A61B 34/25; A61B 34/30; A61B 34/37; A61B 90/36; A61B 90/361; A61B 90/37;
(Continued)

(56) References Cited

U.S. PATENT DOCUMENTS 3,628,535 A   12/1971   Ostrowsky et al.
3,818,284 A    6/1974   DeVersterre et al.
(Continued)

FOREIGN PATENT DOCUMENTS

CA   2682992 A1   11/2008
CN   1846181 A    10/2006
(Continued)

OTHER PUBLICATIONS

Extended European Search Report for Application No. EP23154997.3, mailed on Sep. 28, 2023, 13 pages.
(Continued)

*Primary Examiner* — John R Downey
(74) *Attorney, Agent, or Firm* — Haynes & Boone, LLP.

(57) ABSTRACT

A system comprises a first robotic arm adapted to support and move a tool and a second robotic arm adapted to support and move a camera configured to capture an image of a camera field of view. The system further comprises an input device, a display, and a processor. The processor is configured to display a first synthetic image including a first synthetic image of the tool. The first synthetic image of the tool includes a portion of the tool outside of the camera field of view. The processor is also configured to receive a user input at the input device and responsive to the user input,
(Continued)

change the display of the first synthetic image to a display of a second synthetic image including a second synthetic image of the tool that is different from the first synthetic image of the tool.

20 Claims, 14 Drawing Sheets

Related U.S. Application Data continuation of application No. 16/161,204, filed on Oct. 16, 2018, now Pat. No. 10,737,394, which is a continuation of application No. 15/629,533, filed on Jun. 21, 2017, now Pat. No. 10,137,575, which is a division of application No. 12/415,354, filed on Mar. 31, 2009, now Pat. No. 9,789,608, which is a continuation-in-part of application No. 12/163,087, filed on Jun. 27, 2008, now Pat. No. 10,258,425, and a continuation-in-part of application No. 11/478,531, filed on Jun. 29, 2006, now Pat. No. 9,718,190.

(51) Int. Cl.
*A61B 34/30* (2016.01)
*A61B 34/37* (2016.01)
*A61B 90/00* (2016.01)

(52) U.S. Cl.
CPC ............ *A61B 90/361* (2016.02); *A61B 90/37* (2016.02); *A61B 34/20* (2016.02); *A61B 2034/2059* (2016.02); *A61B 2034/2061* (2016.02); *A61B 2090/371* (2016.02); *G05B 2219/36432* (2013.01); *G05B 2219/39083* (2013.01); *G05B 2219/39096* (2013.01); *G05B 2219/39449* (2013.01); *G05B 2219/40607* (2013.01); *G05B 2219/45117* (2013.01); *G05B 2219/45123* (2013.01)

(58) Field of Classification Search
CPC ............ A61B 34/20; A61B 2034/2059; A61B 2034/2061
See application file for complete search history.

(56) References Cited

U.S. PATENT DOCUMENTS

| | | | |
|---|---|---|---|
| 3,890,552 A | 6/1975 | Devol et al. | |
| 3,905,215 A | 9/1975 | Wright | |
| 3,923,166 A | 12/1975 | Fletcher et al. | |
| 4,150,326 A | 4/1979 | Engelberger et al. | |
| 4,349,837 A | 9/1982 | Hinds | |
| 4,577,621 A | 3/1986 | Patel | |
| 4,588,348 A | 5/1986 | Beni et al. | |
| 4,644,237 A | 2/1987 | Frushour et al. | |
| 4,672,963 A | 6/1987 | Barken | |
| 4,673,988 A | 6/1987 | Jansson et al. | |
| 4,722,056 A | 1/1988 | Roberts et al. | |
| 4,759,074 A | 7/1988 | Iadipaolo et al. | |
| 4,762,455 A | 8/1988 | Coughlan et al. | |
| 4,762,456 A | 8/1988 | Nelson | |
| 4,791,934 A | 12/1988 | Brunnett | |
| 4,815,450 A | 3/1989 | Patel | |
| 4,831,549 A | 5/1989 | Red et al. | |
| 4,833,383 A | 5/1989 | Skarr et al. | |
| 4,837,703 A | 6/1989 | Kakazu et al. | |
| 4,837,734 A | 6/1989 | Ichikawa et al. | |
| 4,839,838 A | 6/1989 | LaBiche et al. | |
| 4,853,874 A | 8/1989 | Iwamoto et al. | |
| 4,858,149 A | 8/1989 | Quarendon | |
| 4,860,215 A | 8/1989 | Seraji | |
| 4,863,133 A | 9/1989 | Bonnell | |
| 4,891,767 A * | 1/1990 | Rzasa | B25J 9/1692 901/30 |
| 4,942,539 A | 7/1990 | McGee et al. | |
| 4,979,949 A | 12/1990 | Matsen, III et al. | |
| 4,984,157 A | 1/1991 | Cline et al. | |
| 4,989,253 A | 1/1991 | Liang et al. | |
| 5,046,022 A | 9/1991 | Conway et al. | |
| 5,053,976 A | 10/1991 | Nose et al. | |
| 5,079,699 A | 1/1992 | Tuy et al. | |
| 5,086,401 A | 2/1992 | Glassman et al. | |
| 5,098,426 A | 3/1992 | Sklar et al. | |
| 5,099,846 A | 3/1992 | Hardy | |
| 5,142,930 A | 9/1992 | Allen et al. | |
| 5,170,347 A | 12/1992 | Tuy et al. | |
| 5,174,276 A | 12/1992 | Crockard | |
| 5,176,702 A | 1/1993 | Bales et al. | |
| 5,182,641 A | 1/1993 | Diner et al. | |
| 5,184,009 A | 2/1993 | Wright et al. | |
| 5,184,601 A | 2/1993 | Putman | |
| 5,187,796 A | 2/1993 | Wang et al. | |
| 5,217,003 A | 6/1993 | Wilk | |
| 5,230,338 A | 7/1993 | Allen et al. | |
| 5,230,623 A | 7/1993 | Guthrie et al. | |
| 5,235,510 A | 8/1993 | Yamada et al. | |
| 5,239,246 A | 8/1993 | Kim | |
| 5,251,127 A | 10/1993 | Raab | |
| 5,251,611 A | 10/1993 | Zehel et al. | |
| 5,257,203 A | 10/1993 | Riley et al. | |
| 5,261,404 A | 11/1993 | Mick et al. | |
| 5,266,875 A | 11/1993 | Slotine et al. | |
| 5,279,309 A | 1/1994 | Taylor et al. | |
| 5,299,288 A | 3/1994 | Glassman et al. | |
| 5,313,306 A | 5/1994 | Kuban et al. | |
| 5,321,353 A | 6/1994 | Furness | |
| 5,337,733 A | 8/1994 | Bauerfeind et al. | |
| 5,341,950 A | 8/1994 | Sinz | |
| 5,343,385 A | 8/1994 | Joskowicz et al. | |
| 5,368,015 A | 11/1994 | Wilk | |
| 5,368,428 A | 11/1994 | Hussey et al. | |
| 5,382,885 A | 1/1995 | Salcudean et al. | |
| 5,397,323 A | 3/1995 | Taylor et al. | |
| 5,402,801 A | 4/1995 | Taylor | |
| 5,408,409 A | 4/1995 | Glassman et al. | |
| 5,417,210 A | 5/1995 | Funda et al. | |
| 5,430,643 A | 7/1995 | Seraji | |
| 5,445,166 A | 8/1995 | Taylor et al. | |
| 5,454,827 A | 10/1995 | Aust et al. | |
| 5,474,571 A | 12/1995 | Lang | |
| 5,482,029 A | 1/1996 | Sekiguchi et al. | |
| 5,493,595 A | 2/1996 | Schoolman | |
| 5,503,320 A | 4/1996 | Webster et al. | |
| 5,515,478 A | 5/1996 | Wang | |
| 5,524,180 A | 6/1996 | Wang et al. | |
| 5,528,955 A | 6/1996 | Hannaford et al. | |
| 5,531,742 A | 7/1996 | Barken | |
| 5,551,432 A | 9/1996 | Iezzi | |
| 5,553,198 A | 9/1996 | Wang et al. | |
| 5,572,999 A | 11/1996 | Funda et al. | |
| 5,601,549 A | 2/1997 | Miyagi | |
| 5,617,858 A | 4/1997 | Taverna et al. | |
| 5,624,390 A | 4/1997 | Van Dyne | |
| 5,624,398 A | 4/1997 | Smith et al. | |
| 5,631,973 A | 5/1997 | Green | |
| 5,638,819 A | 6/1997 | Manwaring et al. | |
| 5,657,429 A | 8/1997 | Wang et al. | |
| 5,695,500 A | 12/1997 | Taylor et al. | |
| 5,704,897 A | 1/1998 | Truppe | |
| 5,715,729 A | 2/1998 | Toyama et al. | |
| 5,737,500 A | 4/1998 | Seraji et al. | |
| 5,748,767 A | 5/1998 | Raab | |
| 5,749,362 A | 5/1998 | Funda et al. | |
| 5,754,741 A | 5/1998 | Wang et al. | |
| 5,755,725 A | 5/1998 | Druais | |
| 5,759,151 A | 6/1998 | Sturges | |
| 5,759,153 A | 6/1998 | Webler et al. | |
| 5,762,458 A | 6/1998 | Wang et al. | |
| 5,765,561 A | 6/1998 | Chen et al. | |
| 5,784,542 A | 7/1998 | Ohm et al. | |
| 5,788,688 A | 8/1998 | Bauer et al. | |

(56) References Cited

U.S. PATENT DOCUMENTS

| | | | |
|---|---|---|---|
| 5,791,231 A | 8/1998 | Cohn et al. |
| 5,792,135 A | 8/1998 | Madhani et al. |
| 5,797,849 A | 8/1998 | Vesely et al. |
| 5,797,900 A | 8/1998 | Madhani et al. |
| 5,807,377 A | 9/1998 | Madhani et al. |
| 5,808,665 A | 9/1998 | Green et al. |
| 5,810,008 A | 9/1998 | Dekel et al. |
| 5,810,880 A | 9/1998 | Jensen et al. |
| 5,814,038 A | 9/1998 | Jensen et al. |
| 5,815,640 A | 9/1998 | Wang et al. |
| 5,817,022 A | 10/1998 | Vesely |
| 5,820,545 A | 10/1998 | Arbter et al. |
| 5,820,623 A | 10/1998 | Ng |
| 5,831,408 A | 11/1998 | Jacobus et al. |
| 5,835,693 A | 11/1998 | Lynch et al. |
| 5,836,880 A | 11/1998 | Pratt |
| 5,841,950 A | 11/1998 | Wang et al. |
| 5,842,473 A | 12/1998 | Fenster et al. |
| 5,842,993 A | 12/1998 | Eichelberger et al. |
| 5,853,367 A | 12/1998 | Chalek et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,887,121 A | 3/1999 | Funda et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Oestensen et al. |
| 5,980,461 A | 11/1999 | Rajan |
| 5,987,591 A | 11/1999 | Jyumonji |
| 5,993,390 A | 11/1999 | Savord et al. |
| 5,993,391 A | 11/1999 | Kamiyama |
| 5,999,662 A | 12/1999 | Burt et al. |
| 6,019,724 A | 2/2000 | Gronningsaeter et al. |
| 6,036,637 A | 3/2000 | Kudo |
| 6,059,718 A | 5/2000 | Taniguchi et al. |
| 6,063,095 A | 5/2000 | Wang et al. |
| 6,072,466 A | 6/2000 | Shah et al. |
| 6,083,170 A | 7/2000 | Ben-Haim |
| 6,084,371 A | 7/2000 | Kress et al. |
| 6,096,025 A | 8/2000 | Borders |
| 6,115,053 A | 9/2000 | Perlin |
| 6,120,433 A | 9/2000 | Mizuno et al. |
| 6,129,670 A | 10/2000 | Burdette et al. |
| 6,184,868 B1 | 2/2001 | Shahoian et al. |
| 6,196,081 B1 | 3/2001 | Yau |
| 6,201,984 B1 | 3/2001 | Funda et al. |
| 6,204,620 B1 | 3/2001 | McGee et al. |
| 6,224,542 B1 | 5/2001 | Chang et al. |
| 6,226,566 B1 | 5/2001 | Funda et al. |
| 6,241,725 B1 | 6/2001 | Cosman |
| 6,243,624 B1 | 6/2001 | Wu et al. |
| 6,246,200 B1 | 6/2001 | Blumenkranz et al. |
| 6,256,529 B1 | 7/2001 | Holupka et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |
| 6,330,837 B1 | 12/2001 | Charles et al. |
| 6,331,181 B1 | 12/2001 | Tierney et al. |
| 6,342,889 B1 | 1/2002 | Callahan |
| 6,358,749 B1 | 3/2002 | Orthman |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,425,865 B1 | 7/2002 | Salcudean et al. |
| 6,434,416 B1 | 8/2002 | Mizoguchi et al. |
| 6,436,107 B1 | 8/2002 | Wang et al. |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,491,701 B2 | 12/2002 | Tierney et al. |
| 6,493,608 B1 | 12/2002 | Niemeyer |
| 6,522,906 B1 * | 2/2003 | Salisbury, Jr. ........ A61B 1/0005 600/407 |
| 6,522,908 B1 | 2/2003 | Miyashita et al. |
| 6,547,782 B1 | 4/2003 | Taylor |
| 6,550,757 B2 | 4/2003 | Sesek |
| 6,569,084 B1 | 5/2003 | Mizuno et al. |
| 6,574,355 B2 | 6/2003 | Green |
| 6,594,522 B1 | 7/2003 | Korenaga |
| 6,594,552 B1 | 7/2003 | Nowlin et al. |
| 6,599,247 B1 | 7/2003 | Stetten |
| 6,602,185 B1 | 8/2003 | Uchikubo |
| 6,620,173 B2 | 9/2003 | Gerbi et al. |
| 6,642,836 B1 | 11/2003 | Wang et al. |
| 6,643,563 B2 | 11/2003 | Hosek et al. |
| 6,645,196 B1 | 11/2003 | Nixon et al. |
| 6,648,816 B2 | 11/2003 | Irion et al. |
| 6,654,031 B1 | 11/2003 | Ito et al. |
| 6,656,110 B1 | 12/2003 | Irion et al. |
| 6,659,939 B2 * | 12/2003 | Moll ..................... A61B 34/35 600/102 |
| 6,665,554 B1 | 12/2003 | Charles et al. |
| 6,671,581 B2 | 12/2003 | Niemeyer et al. |
| 6,676,669 B2 | 1/2004 | Charles et al. |
| 6,699,177 B1 | 3/2004 | Wang et al. |
| 6,702,736 B2 | 3/2004 | Chen et al. |
| 6,714,839 B2 | 3/2004 | Salisbury, Jr. et al. |
| 6,765,569 B2 | 7/2004 | Neumann et al. |
| 6,770,081 B1 | 8/2004 | Cooper et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,712 B2 | 12/2004 | Tovey et al. |
| 6,837,883 B2 | 1/2005 | Moll et al. |
| 6,847,922 B1 | 1/2005 | Wampler, II |
| 6,852,107 B2 | 2/2005 | Wang et al. |
| 6,866,671 B2 | 3/2005 | Tierney et al. |
| 6,876,891 B1 | 4/2005 | Schuler et al. |
| 6,899,672 B2 | 5/2005 | Chin et al. |
| 6,905,460 B2 | 6/2005 | Wang et al. |
| 6,926,709 B2 | 8/2005 | Bieger et al. |
| 6,960,162 B2 | 11/2005 | Saadat et al. |
| 6,984,203 B2 | 1/2006 | Tartaglia et al. |
| 6,991,627 B2 | 1/2006 | Madhani et al. |
| 7,041,053 B2 | 5/2006 | Miyake |
| 7,107,090 B2 | 9/2006 | Salisbury et al. |
| 7,107,124 B2 | 9/2006 | Green |
| 7,118,582 B1 | 10/2006 | Wang et al. |
| 7,144,367 B2 | 12/2006 | Chen et al. |
| 7,155,315 B2 | 12/2006 | Niemeyer et al. |
| 7,155,316 B2 | 12/2006 | Sutherland et al. |
| 7,181,315 B2 | 2/2007 | Watanabe et al. |
| 7,194,118 B1 | 3/2007 | Harris et al. |
| 7,211,978 B2 | 5/2007 | Chang et al. |
| 7,297,142 B2 | 11/2007 | Brock |
| 7,302,288 B1 | 11/2007 | Schellenberg et al. |
| 7,413,565 B2 | 8/2008 | Wang et al. |
| 7,491,198 B2 | 2/2009 | Kockro |
| 7,493,153 B2 | 2/2009 | Ahmed et al. |
| 7,574,250 B2 | 8/2009 | Niemeyer |
| 7,725,214 B2 | 5/2010 | Diolaiti |
| 7,806,891 B2 | 10/2010 | Nowlin et al. |
| 7,819,859 B2 | 10/2010 | Prisco et al. |
| 7,833,156 B2 | 11/2010 | Williams et al. |
| 7,865,266 B2 | 1/2011 | Moll et al. |
| 7,963,913 B2 | 6/2011 | Devengenzo et al. |
| 7,967,813 B2 | 6/2011 | Cooper et al. |
| 7,979,157 B2 | 7/2011 | Anvari |
| 7,996,110 B2 | 8/2011 | Lipow et al. |

(56) References Cited

U.S. PATENT DOCUMENTS

| | | |
|---|---|---|
| 7,998,058 B2 | 8/2011 | Kura et al. |
| 8,004,229 B2 | 8/2011 | Nowlin et al. |
| 8,005,571 B2 | 8/2011 | Sutherland et al. |
| 8,016,749 B2 | 9/2011 | Clerc et al. |
| 8,062,288 B2 | 11/2011 | Cooper et al. |
| 8,108,072 B2 | 1/2012 | Zhao et al. |
| 8,120,301 B2 | 2/2012 | Goldberg et al. |
| 8,130,907 B2 | 3/2012 | Maurer, Jr. et al. |
| 8,142,447 B2 | 3/2012 | Cooper et al. |
| 8,155,479 B2 | 4/2012 | Hoffman et al. |
| 8,170,716 B2 | 5/2012 | Coste-Maniere et al. |
| 8,175,861 B2 | 5/2012 | Huang et al. |
| 8,221,304 B2 | 7/2012 | Shioda et al. |
| 8,244,443 B2 | 8/2012 | Oshima et al. |
| 8,256,319 B2 | 9/2012 | Cooper et al. |
| 8,306,656 B1 | 11/2012 | Schaible et al. |
| 8,315,720 B2 | 11/2012 | Mohr et al. |
| 8,335,590 B2 | 12/2012 | Costa et al. |
| 8,398,541 B2 | 3/2013 | Dimaio et al. |
| 8,419,717 B2 | 4/2013 | Diolaiti et al. |
| 8,541,970 B2 | 9/2013 | Nowlin et al. |
| 8,554,368 B2 | 10/2013 | Fielding et al. |
| 8,597,280 B2 | 12/2013 | Cooper et al. |
| 8,620,473 B2 | 12/2013 | Diolaiti et al. |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,801,601 B2 | 8/2014 | Prisco et al. |
| 8,816,628 B2 | 8/2014 | Nowlin et al. |
| 8,823,308 B2 | 9/2014 | Nowlin et al. |
| 8,864,652 B2 | 10/2014 | Diolaiti et al. |
| 8,864,751 B2 | 10/2014 | Prisco et al. |
| 8,903,546 B2 | 12/2014 | Diolaiti et al. |
| 8,918,211 B2 | 12/2014 | Diolaiti et al. |
| 8,944,070 B2 | 2/2015 | Guthart et al. |
| 9,084,623 B2 | 7/2015 | Gomez et al. |
| 9,089,256 B2 | 7/2015 | Tognaccini et al. |
| 9,101,397 B2 | 8/2015 | Guthart et al. |
| 9,138,129 B2 | 9/2015 | Diolaiti |
| 9,232,984 B2 | 1/2016 | Guthart et al. |
| 9,259,283 B2 | 2/2016 | Ogawa et al. |
| 9,333,042 B2 | 5/2016 | Diolaiti et al. |
| 9,345,387 B2 | 5/2016 | Larkin |
| 9,387,048 B2 | 7/2016 | Donhowe et al. |
| 9,469,034 B2 | 10/2016 | Diolaiti et al. |
| 9,492,927 B2 | 11/2016 | Diolaiti et al. |
| 9,516,996 B2 | 12/2016 | Diolaiti et al. |
| 9,526,587 B2 | 12/2016 | Zhao et al. |
| 9,565,990 B2 | 2/2017 | Lee et al. |
| 9,622,826 B2 | 4/2017 | Diolaiti et al. |
| 9,629,520 B2 | 4/2017 | Diolaiti |
| 9,717,563 B2 | 8/2017 | Tognaccini et al. |
| 9,718,190 B2 | 8/2017 | Larkin et al. |
| 9,788,909 B2 | 10/2017 | Larkin et al. |
| 9,789,608 B2 | 10/2017 | Itkowitz et al. |
| 9,795,446 B2 | 10/2017 | Dimaio et al. |
| 9,801,690 B2 | 10/2017 | Larkin et al. |
| 9,901,408 B2 | 2/2018 | Larkin |
| 9,949,798 B2 | 4/2018 | Weir et al. |
| 9,956,044 B2 | 5/2018 | Gomez et al. |
| 10,008,017 B2 | 6/2018 | Itkowitz et al. |
| 10,137,575 B2 | 11/2018 | Itkowitz et al. |
| 10,188,472 B2 | 1/2019 | Diolaiti et al. |
| 10,258,425 B2 | 4/2019 | Mustufa et al. |
| 10,271,909 B2 | 4/2019 | Guthart et al. |
| 10,271,912 B2 | 4/2019 | Diolaiti et al. |
| 10,271,915 B2 | 4/2019 | Diolaiti et al. |
| 10,282,881 B2 | 5/2019 | Itkowitz et al. |
| 10,368,952 B2 | 8/2019 | Tognaccini et al. |
| 10,433,919 B2 | 10/2019 | Guthart et al. |
| 10,507,066 B2 | 12/2019 | DiMaio et al. |
| 10,537,994 B2 | 1/2020 | Diolaiti et al. |
| 10,695,136 B2 | 6/2020 | Larkin |
| 10,730,187 B2 | 8/2020 | Larkin et al. |
| 10,737,394 B2 | 8/2020 | Itkowitz et al. |
| 10,772,689 B2 | 9/2020 | Gomez et al. |
| 10,773,388 B2 | 9/2020 | Larkin et al. |
| 10,828,774 B2 | 11/2020 | Diolaiti et al. |
| 10,959,798 B2 | 3/2021 | Diolaiti et al. |
| 10,984,567 B2 | 4/2021 | Itkowitz et al. |
| 11,382,702 B2 | 7/2022 | Tognaccini et al. |
| 11,389,255 B2 | 7/2022 | DiMaio et al. |
| 11,399,908 B2 | 8/2022 | Diolaiti et al. |
| 11,432,888 B2 | 9/2022 | Diolaiti et al. |
| 11,596,490 B2 | 3/2023 | Diolaiti et al. |
| 11,638,622 B2 | 5/2023 | Mustufa et al. |
| 11,638,999 B2 | 5/2023 | Itkowitz et al. |
| 11,751,955 B2 | 9/2023 | Diolaiti et al. |
| 11,806,102 B2 | 11/2023 | Dimaio et al. |
| 11,865,729 B2 | 1/2024 | Larkin et al. |
| 11,941,734 B2 | 3/2024 | Itkowitz et al. |
| 12,097,002 B2 | 9/2024 | Diolaiti et al. |
| 2001/0035871 A1 | 11/2001 | Bieger et al. |
| 2002/0044104 A1 | 4/2002 | Friedrich et al. |
| 2002/0045888 A1 | 4/2002 | Ramans et al. |
| 2002/0089544 A1 | 7/2002 | Jahn et al. |
| 2002/0120188 A1 | 8/2002 | Brock et al. |
| 2002/0128552 A1 | 9/2002 | Nowlin et al. |
| 2002/0156345 A1 | 10/2002 | Eppler et al. |
| 2002/0193800 A1 | 12/2002 | Kienzle, III et al. |
| 2003/0023347 A1 | 1/2003 | Konno et al. |
| 2003/0032878 A1 | 2/2003 | Shahidi |
| 2003/0055410 A1 | 3/2003 | Evans et al. |
| 2003/0060927 A1 | 3/2003 | Gerbi et al. |
| 2003/0109780 A1* | 6/2003 | Coste-Maniere ...... G06T 7/0012 600/407 |
| 2003/0114730 A1 | 6/2003 | Hale et al. |
| 2003/0114962 A1* | 6/2003 | Niemeyer ............. A61B 34/30 700/250 |
| 2003/0144649 A1 | 7/2003 | Ghodoussi et al. |
| 2003/0167103 A1 | 9/2003 | Tang et al. |
| 2003/0225479 A1 | 12/2003 | Waled |
| 2004/0024311 A1 | 2/2004 | Quaid, III |
| 2004/0034283 A1 | 2/2004 | Quaid et al. |
| 2004/0039485 A1 | 2/2004 | Niemeyer et al. |
| 2004/0044295 A1* | 3/2004 | Reinert ................. G16H 20/40 600/587 |
| 2004/0046711 A1 | 3/2004 | Triebfuerst |
| 2004/0046916 A1 | 3/2004 | Lyu et al. |
| 2004/0049205 A1 | 3/2004 | Lee et al. |
| 2004/0077940 A1 | 4/2004 | Kienzle et al. |
| 2004/0106916 A1 | 6/2004 | Quaid et al. |
| 2004/0138700 A1 | 7/2004 | Cooper et al. |
| 2004/0176751 A1 | 9/2004 | Weitzner et al. |
| 2004/0189675 A1 | 9/2004 | Pretlove et al. |
| 2004/0210105 A1 | 10/2004 | Hale et al. |
| 2004/0225183 A1 | 11/2004 | Michlitsch et al. |
| 2004/0238732 A1 | 12/2004 | State et al. |
| 2004/0243147 A1 | 12/2004 | Lipow |
| 2004/0249508 A1 | 12/2004 | Suita et al. |
| 2004/0254454 A1 | 12/2004 | Kockro |
| 2004/0254679 A1 | 12/2004 | Nagasaka |
| 2005/0022158 A1 | 1/2005 | Launay et al. |
| 2005/0054895 A1 | 3/2005 | Hoeg et al. |
| 2005/0059960 A1 | 3/2005 | Simaan et al. |
| 2005/0096502 A1 | 5/2005 | Khalili |
| 2005/0096892 A1 | 5/2005 | Watanabe et al. |
| 2005/0107680 A1 | 5/2005 | Kopf et al. |
| 2005/0113640 A1 | 5/2005 | Saadat et al. |
| 2005/0166413 A1 | 8/2005 | Crampton et al. |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2005/0267359 A1 | 12/2005 | Hussaini et al. |
| 2005/0273198 A1 | 12/2005 | Bischoff |
| 2006/0013523 A1 | 1/2006 | Childlers et al. |
| 2006/0058988 A1 | 3/2006 | Defranoux et al. |
| 2006/0079108 A1 | 4/2006 | McCoy |
| 2006/0142657 A1* | 6/2006 | Quaid .................... A61B 90/37 600/424 |
| 2006/0149129 A1 | 7/2006 | Watts et al. |
| 2006/0149418 A1* | 7/2006 | Anvari .................. A61B 34/74 700/245 |

(56) References Cited

U.S. PATENT DOCUMENTS

| | | |
|---|---|---|
| 2006/0161045 A1 | 7/2006 | Merril et al. |
| 2006/0161138 A1 | 7/2006 | Orban et al. |
| 2006/0178559 A1 | 8/2006 | Kumar et al. |
| 2006/0258938 A1 | 11/2006 | Hoffman et al. |
| 2006/0261770 A1 | 11/2006 | Kishi et al. |
| 2006/0293592 A1 | 12/2006 | Jensen |
| 2007/0016174 A1 | 1/2007 | Millman et al. |
| 2007/0021738 A1 | 1/2007 | Hasser et al. |
| 2007/0038080 A1 | 2/2007 | Salisbury, Jr. et al. |
| 2007/0060879 A1 | 3/2007 | Weitzner et al. |
| 2007/0071310 A1 | 3/2007 | Kobayashi et al. |
| 2007/0081714 A1 | 4/2007 | Wallack et al. |
| 2007/0106307 A1 | 5/2007 | Bodduluri et al. |
| 2007/0135803 A1 | 6/2007 | Belson |
| 2007/0138992 A1 | 6/2007 | Prisco et al. |
| 2007/0142825 A1 | 6/2007 | Prisco et al. |
| 2007/0142968 A1 | 6/2007 | Prisco et al. |
| 2007/0144298 A1 | 6/2007 | Miller |
| 2007/0151389 A1 | 7/2007 | Prisco et al. |
| 2007/0156019 A1 | 7/2007 | Larkin et al. |
| 2007/0156285 A1 | 7/2007 | Sillman et al. |
| 2007/0167801 A1 | 7/2007 | Webler et al. |
| 2007/0177009 A1 | 8/2007 | Bayer et al. |
| 2007/0197896 A1 | 8/2007 | Moll et al. |
| 2007/0229015 A1 | 10/2007 | Yoshida et al. |
| 2007/0255454 A1 | 11/2007 | Dariush |
| 2007/0265491 A1 | 11/2007 | Krag et al. |
| 2007/0265495 A1 | 11/2007 | Vayser |
| 2007/0270650 A1 | 11/2007 | Eno et al. |
| 2007/0270685 A1 | 11/2007 | Kang et al. |
| 2007/0283970 A1 | 12/2007 | Mohr et al. |
| 2007/0287884 A1 | 12/2007 | Schena |
| 2007/0287889 A1 | 12/2007 | Mohr |
| 2007/0296366 A1 | 12/2007 | Quaid et al. |
| 2007/0299387 A1 | 12/2007 | Williams et al. |
| 2008/0033240 A1 | 2/2008 | Hoffman et al. |
| 2008/0045800 A2 | 2/2008 | Farr |
| 2008/0051629 A1 | 2/2008 | Sugiyama et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin et al. |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0081992 A1 | 4/2008 | Kagermeier |
| 2008/0091302 A1 | 4/2008 | Sholev |
| 2008/0118115 A1 | 5/2008 | Williamson et al. |
| 2008/0119824 A1 | 5/2008 | Weitzner et al. |
| 2008/0140087 A1 | 6/2008 | Barbagli |
| 2008/0151041 A1 | 6/2008 | Shafer et al. |
| 2008/0161830 A1 | 7/2008 | Sutherland et al. |
| 2008/0188986 A1 | 8/2008 | Hoppe |
| 2008/0221591 A1* | 9/2008 | Farritor ............... A61B 34/70 606/130 |
| 2008/0243142 A1 | 10/2008 | Gildenberg |
| 2008/0247506 A1 | 10/2008 | Maschke |
| 2008/0269862 A1 | 10/2008 | Elmouelhi et al. |
| 2008/0287963 A1 | 11/2008 | Rogers et al. |
| 2009/0005640 A1 | 1/2009 | Fehre et al. |
| 2009/0012531 A1 | 1/2009 | Quaid et al. |
| 2009/0024142 A1 | 1/2009 | Ruiz Morales |
| 2009/0088634 A1 | 4/2009 | Zhao et al. |
| 2009/0105750 A1 | 4/2009 | Price et al. |
| 2009/0192523 A1 | 7/2009 | Larkin et al. |
| 2009/0228145 A1 | 9/2009 | Hodgson et al. |
| 2009/0248036 A1 | 10/2009 | Hoffman et al. |
| 2009/0259105 A1 | 10/2009 | Miyano et al. |
| 2009/0326322 A1 | 12/2009 | Diolaiti |
| 2009/0326552 A1 | 12/2009 | Diolaiti |
| 2009/0326711 A1 | 12/2009 | Chang et al. |
| 2010/0004505 A1 | 1/2010 | Umemoto et al. |
| 2010/0036198 A1 | 2/2010 | Tacchino et al. |
| 2010/0106356 A1 | 4/2010 | Trepagnier et al. |
| 2010/0169815 A1 | 7/2010 | Zhao et al. |
| 2010/0198232 A1 | 8/2010 | Diolaiti |
| 2010/0228264 A1 | 9/2010 | Robinson et al. |
| 2010/0249657 A1 | 9/2010 | Nycz et al. |
| 2010/0298839 A1 | 11/2010 | Castro |
| 2010/0317965 A1 | 12/2010 | Itkowitz et al. |
| 2010/0328363 A1 | 12/2010 | Nakanishi |
| 2010/0331855 A1 | 12/2010 | Zhao et al. |
| 2010/0331856 A1 | 12/2010 | Carlson et al. |
| 2010/0332033 A1 | 12/2010 | Diolaiti et al. |
| 2011/0071675 A1 | 3/2011 | Wells et al. |
| 2011/0196199 A1 | 8/2011 | Donhowe et al. |
| 2011/0258568 A1 | 10/2011 | Pandurangan et al. |
| 2011/0290856 A1 | 12/2011 | Shelton, IV et al. |
| 2011/0313573 A1 | 12/2011 | Schreiber et al. |
| 2012/0132450 A1 | 5/2012 | Timm et al. |
| 2012/0154564 A1 | 6/2012 | Hoffman et al. |
| 2013/0178868 A1 | 7/2013 | Roh |
| 2013/0289767 A1 | 10/2013 | Lim et al. |
| 2013/0289768 A1 | 10/2013 | Yeung et al. |
| 2014/0052150 A1 | 2/2014 | Taylor et al. |
| 2015/0032126 A1 | 1/2015 | Nowlin et al. |
| 2015/0051733 A1 | 2/2015 | Nowlin et al. |
| 2017/0210012 A1 | 7/2017 | Larkin et al. |
| 2018/0297206 A1 | 10/2018 | Larkin et al. |
| 2019/0090967 A1 | 3/2019 | Guthart et al. |
| 2019/0209262 A1 | 7/2019 | Mustufa et al. |
| 2020/0331147 A1 | 10/2020 | Larkin et al. |
| 2021/0059780 A1 | 3/2021 | Sutherland et al. |
| 2021/0153964 A1 | 5/2021 | Diolaiti et al. |
| 2021/0256749 A1 | 8/2021 | Itkowitz et al. |
| 2021/0290326 A1 | 9/2021 | Diolaiti et al. |
| 2022/0296317 A1 | 9/2022 | Dimaio et al. |
| 2022/0354600 A1 | 11/2022 | Tognaccini et al. |
| 2022/0361969 A1 | 11/2022 | Diolaiti et al. |
| 2023/0225803 A1 | 7/2023 | Mustufa et al. |
| 2023/0363838 A1 | 11/2023 | Diolaiti et al. |
| 2024/0296608 A1 | 9/2024 | Itkowitz et al. |
| 2024/0407873 A1 | 12/2024 | Diolaiti et al. |

FOREIGN PATENT DOCUMENTS

| | | |
|---|---|---|
| CN | 1879574 A | 12/2006 |
| CN | 101160104 A | 4/2008 |
| CN | 101184429 A | 5/2008 |
| CN | 101530347 A | 9/2009 |
| CN | 101594816 A | 12/2009 |
| CN | 101610712 A | 12/2009 |
| EP | 514584 A2 | 11/1992 |
| EP | 0646358 A1 | 4/1995 |
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| EP | 1269389 B1 | 9/2005 |
| EP | 1131004 B1 | 10/2009 |
| JP | H01280449 A | 11/1989 |
| JP | H01310875 A | 12/1989 |
| JP | H04231034 A | 8/1992 |
| JP | H07184923 A | 7/1995 |
| JP | H07265321 A | 10/1995 |
| JP | H0889506 A | 4/1996 |
| JP | H08107875 A | 4/1996 |
| JP | H08132372 A | 5/1996 |
| JP | H08154321 A | 6/1996 |
| JP | H08215211 A | 8/1996 |
| JP | H08224241 A | 9/1996 |
| JP | H08275958 A | 10/1996 |

(56) References Cited

FOREIGN PATENT DOCUMENTS

| | | |
|---|---|---|
| JP | H08299363 A | 11/1996 |
| JP | H09141580 A | 6/1997 |
| JP | H10146341 A | 6/1998 |
| JP | H11309 A | 1/1999 |
| JP | 2000500679 A | 1/2000 |
| JP | 2000300579 A | 10/2000 |
| JP | 2001000448 A | 1/2001 |
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 3539645 B2 | 7/2004 |
| JP | 2004223128 A | 8/2004 |
| JP | 3587830 B2 | 11/2004 |
| JP | 2005110878 A | 4/2005 |
| JP | 2005135278 A | 5/2005 |
| JP | 2005303327 A | 10/2005 |
| JP | 2005334650 A | 12/2005 |
| JP | 2007029232 A | 2/2007 |
| JP | 2007090481 A | 4/2007 |
| JP | 2007508913 A | 4/2007 |
| JP | 2007276052 A | 10/2007 |
| JP | 2007531553 A | 11/2007 |
| JP | 2008173724 A | 7/2008 |
| JP | 2009006410 A | 1/2009 |
| JP | 2009012106 A | 1/2009 |
| JP | 2009039814 A | 2/2009 |
| JP | 2009525097 A | 7/2009 |
| JP | 4354042 B2 | 10/2009 |
| JP | 2009537229 A | 10/2009 |
| JP | 4883563 B2 | 2/2012 |
| WO | WO-9501757 A1 | 1/1995 |
| WO | WO-9507055 A1 | 3/1995 |
| WO | WO-9729690 A1 | 8/1997 |
| WO | WO-9743942 A1 | 11/1997 |
| WO | WO-9743943 A1 | 11/1997 |
| WO | WO-9823216 A1 | 6/1998 |
| WO | WO-0030548 A1 | 6/2000 |
| WO | WO-03061482 A1 | 7/2003 |
| WO | WO-2004014244 A2 | 2/2004 |
| WO | WO-2004114037 A2 | 12/2004 |
| WO | WO-2005037120 A1 | 4/2005 |
| WO | WO-2005039391 A2 | 5/2005 |
| WO | WO-2005043319 A2 | 5/2005 |
| WO | WO-2006079108 A1 | 7/2006 |
| WO | WO-2006091494 A1 | 8/2006 |
| WO | WO-2006124390 A2 | 11/2006 |
| WO | WO-2007005555 A2 | 1/2007 |
| WO | WO-2007012185 A1 | 2/2007 |
| WO | WO-2007030173 A1 | 3/2007 |
| WO | WO-2007047782 A2 | 4/2007 |
| WO | WO-2007088206 A2 | 8/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008065581 A2 | 6/2008 |
| WO | WO-2008094766 A2 | 8/2008 |
| WO | WO-2008103383 A1 | 8/2008 |
| WO | WO-2009034477 A2 | 3/2009 |
| WO | WO-2009037576 A2 | 3/2009 |
| WO | WO-2009044287 A2 | 4/2009 |
| WO | WO-2009158164 A1 | 12/2009 |
| WO | WO-2010039394 A1 | 4/2010 |
| WO | WO-2010040685 A1 | 4/2010 |

OTHER PUBLICATIONS

3D Slicer, http://slicer.org/welcome.html , downloaded Oct. 25, 2006, p. 1; and Introduction, http://slicer.org/intro/index.html , downloaded Oct. 25, 2006, pp. 1-4.

Abolmaesumi, Purang et al., "A User Interface for Robot-Assisted Diagnostic Ultrasound," IEEE Robotics and Automation Conference, 2001, pp. 1549-1554, vol. 2, IEEE.

Abolmaesumi, Purang et al., "Image Guided Control of a Robot for Medical Ultrasound," IEEE Transactions on Robotics and Automation, 2002, pp. 11-23, vol. 18—Issue 1, IEEE.

Adams, Ludwig et al., "Computer-Assisted Surgery," IEEE Computer Graphics & Applications, May 1990, pp. 43-52, vol. 10—Issue 3, IEEE Computer Society Press.

Ahlering, Thomas. E. et al., "Robotic radical prostatectomy: a technique to reduce pT2 positive margins," Urology, 2004, pp. 1224-1228, vol. 64 Issue 6, Elsevier Inc.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26, 1984, pp. 40-45, vol. 1.

Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.

Askew R.S., et al., "Ground Control Testbed for Space Station Freedom Robot Manipulators," IEEE Virtual Reality Annual International Symposium, 1993, pp. 69-75.

Azuma et al., "Recent Advances in Augmented Reality," IEEE Computer Graphics and Applications, Dec. 2001, 14 pages.

Azuma, Ronald T., "A Survey of Augmented Reality," Teleoperators and Virtual Environments, 1997, pp. 355-385, vol. 6—No. 4.

Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

Banovac, F., et al., "Liver Tumor Biopsy in a Respiring Phantom with the Assistance of a Novel Electromagnetic Navigation Device," Springer-Verlag, 2002, pp. 200-207.

Bartels, Richard H. et al., "An Introduction to Splines for use in Computer Graphics and Geometric Modeling," 1987, 6 Pages total, Morgan kaufmann publishers, Inc.

Bartels, Richard H. et al., "Solution of the Matrix Equation AX+XB=C," Communications of the ACM, 1972, pp. 820-826, vol. 15—Issue 9, ACM Press.

Baumann, Roger, "Haptic Interface for Virtual Reality Based Laparoscopic Surgery Training Environment," These No. 1734 Ecole Pholytechnique Federale de Lausanne, 1997, 104 Total Pages.

Bejczy, Antal K. et al., "Controlling Remote Manipulators through Kinesthetic Coupling," Computers in Mechanical Engineering, 1983, pp. 48-60, vol. 1—Issue 1.

Ben Gayed, M. et al., "An Advanced Control Micromanipulator for Surgical Applications," Systems Science, 1987, pp. 123-134, vol. 13.

Berkelman, Peter J. et al., "A Compact Compliant Laparoscopic Endoscope Manipulator," IEEE International Conference on Robotics and Automation, 2002, pp. 1870-1875, vol. 2, IEEE.

Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.

Berkelman, Peter J. et al., "A miniature microsurgical instrument tip force sensor for enhanced force feedback during robot-assisted manipulation," IEEE Transactions on Robotics and Automation, 2000, pp. 917-922, vol. 19—Issue 5, IEEE.

Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.

(56) References Cited

OTHER PUBLICATIONS

Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.

Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.

Bettini, Alessandro et al., "Vision Assisted Control for Manipulation Using Virtual Fixtures," IEEE Transactions on Robotics, 2004, pp. 953-966, vol. 20—Issue 6, IEEE.

Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.

Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.

Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.

Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.

Boctor, Emad, M. et al., "CISUS: An integrated 3D ultrasound system for IGT using a modular tracking API," Proceedings of the SPIE, 2004, pp. 247-256, vol. 5367, SPIE.

Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.

Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science, 2001, pp. 13-22, vol. 2074, Springer.

Boctor, Emad, M. et al., "Robot-assisted 3D strain imaging for monitoring thermal ablation of liver," Annual congress of the Society of American Gastrointestinal Endoscopic Surgeons (SAGES), Emerging Technology Lunch Poster TP004, 2005, pp. 240-241.

Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.

Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.

Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.

Borovoi, A.V., "Stability of a manipulator with force feedback," Izv. AN SSSR Mekhanika Tverdogo Teal, 1990, pp. 37-45, vol. 25—Issue 1, Allerton Press, Inc.

Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.

Brown, Myron M. et al., "Advances in Computational Stereo," IEEE Transactions on Pattern Analysis and Machine Intelligence (PAMI), 2003, pp. 993-1008, vol. 25 Issue, IEEE.

Burdea, Grigore et al., "Dextrous Telerobotics with Force Feedback—an overview. Part 2: Control and Implementation," Robotica, 1991, pp. 291-298, vol. 9.

Burschka, D., et al., "Navigating Inner Space: 3-D Assistance for Minimally Invasive Surgery," Robotics and Autonomous Systems, 2005, vol. 52(1), pp. 5-26.

Burschka, Darius et al., "Scale-Invariant Registration of Monocular Endoscopic Images to CT-Scans for Sinus Surgery," Med Image Anal, 2004, pp. 413-421, vol. 2, Springer-Verlag.

Burschka, Darius et al., "Scale-Invariant Registration of Monocular Stereo Images to 3D Surface Models," IEEE Int. Conf. on Robots and Systems, 2004, pp. 2581-2586, vol. 3, IEEE.

Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.

Bzostek, Andrew, "Computer-Integrated needle therapy systems: Implementation and Analysis," Computer Science, 2005, 379 pages.

Bzostek, Andrew et al., "A Testbed System for Robotically Assisted Percutaneous Pattern Therapy," Medical Image Computing and Computer-Assisted Surgery, Lecture Notes in Computer Science, 1999, pp. 1098-1107, vol. 1679, Springer.

Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.

Bzostek, Andrew, "Image Guided Percutaneous Pattern Placement in Soft Tissue," The Johns Hopkins University Dept. of Computer Science: Baltimore, 1997, pp. 2007-01-22.

Cadeddu, Jeffrey A. et al., "A Robotic System for Percutaneous Renal Access," The Journal of Urology, 1997, pp. 1589-1593, vol. 158—Issue 4.

Cadeddu, Jeffrey et al., "A robotic system for percutaneous renal access incorporating a remote center of motion design," Journal of Endourolog, 1998, S237, vol. 12.

Cannon, Jeremy W. et al., "Real-time three-dimensional ultrasound for guiding surgical tasks," Computer Aided Surgery, 2003, pp. 82-90, vol. 8—No. 2, John Wiley & Sons.

Cao, Caroline L., et al., "Task and motion analysis in endoscopic surgery," Submitted for Fifth Annual Symposium on Haptic Interfaces for Virtual Environment and Teloperator Systems for the Winter Meeting of ASME, 1996, pp. 1-32.

Carr, J., "Surface reconstruction in 3D medical imaging," PhD Thesis, Part 1, University of Canterbury, Christchurch, New Zealand, 1996, 112 Pages.

Carr, J., "Surface reconstruction in 3D medical imaging," PhD Thesis, Part 2, University of Canterbury, Christchurch, New Zealand, 1996, 112 Pages.

Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.

Chang, Jun Keun et al., "Intravascular micro active catheter for minimal invasive surgery," 1st Annual International Conference on Microtechnologies in Medicine and Biology, 2000, pp. 243-246.

Chen, Homer H. "A Screw Motion Approach to Uniqueness Analysis of Head-Eye Geometry," Computer Vision and Pattern Recognition, 1991, pp. 145-151, IEEE.

Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.

Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.

Choti, Michael A., "Hepatic Radiofrequency Ablation," Cancer Journal, 2000, pp. S291-S292, vol. 6—issue 4, Jones and Bartlett.

Choti, Michael A., "Surgical Management of Hepatocellular Carcinoma: Resection and Ablation," Journal of Vascular and Interventional Radiology, 2002, pp. S197-S203, vol. 13—No. 9.

(56) References Cited

OTHER PUBLICATIONS

Christensen, B. et al., "Model based sensor directed remediation of underground storage tanks," International Conf. on Robotics and Automation, Sacramento, CA, Apr. 1991, pp. 1377-1383, vol. 2. IEEE.
Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary, Kevin et al., "State of the Art in Surgical Robotics:Clinical Applications and Technology Challenges," Computer Aided Surgery, 2001 [retrieved on Feb. 24, 2002], pp. 1-26.
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 page, vol. 221—No. 618.
Colgate J.E., "Power and Impedance Scaling in Bilateral Manipulation," IEEE International Conference on Robotics and Automation, Sacramento, California, Apr. 1991, vol. 3, pp. 2292-2297.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 1999, pp. 286-298, vol. 18 (3), Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.
Davies, S.C., et al., "Ultrasound Quantitaion of Respiratory Organ Motion in the Upper Abdomen," British Journal of Radiology, Nov. 1994, vol. 67 (803), pp. 1096-1102.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Debus, Thomas et al., "Multichannel Vibrotactile Display for Sensory Substitution During Teleoperation," Proc. SPIE Telemanipulator and Telepresence Technologies VIII, 2001, pp. 42-49, vol. 4570, SPIE.
Degoulange, E. et al., "Hippocrate: an intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 3217, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra-Operative Treatment Planning: Permanent Seed Brachytherapy," 2000, p. 4.
Dolan, J.M. et al., "A Robot in an Operating Room: A Bull in a China Shop?," IEEE Proceedings of the Ninth Annual Conference of the IEEE Engineering in Medicine and Biology Society, Nov. 1987, vol. 2, pp. 1096-1097.
Elder, Matthew C. et al., "Specifying user interfaces for safety critical medical systems," Second Annual International Symposium on Medical Robotics and Computer Assisted Surgery, Nov. 1995, pp. 148-155.

Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Extended European Search Report for Application No. EP21158299.4 mailed on May 21, 2021, 09 pages.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging, San Diego, California, Published in SPIE: Medical Physics, Feb. 20-26, 1999, pp. 2-11, vol. 3859, SPIE.
Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.
Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.
Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.
Fisher, Scott S., "Virtual interface environment," IEEE/A1AA 7th Digital Avionics Systems Conference Ft. Worth Texas, 1986, pp. 346-350, IEEE.
Frantz D.D. et al., "Accuracy assessment protocols for electromagnetic tracking systems," Physics in Medicine and Biology, 2003, pp. 2241-2251, Issue 48.
Fu, K.S. et al., "Robotics: control, sensing, vision, and intelligence," 1987, pp. 12-76 and 201-265, Ch. 2 & 5, McGraw-Hill Book Company.
Fuchs, Henry et al., "Augmented Reality Visualization for Laparoscopic Surgery," Medical Image Computing and Computer-Assisted Intervention, 1998, pp. 934-943, vol. 1496, Springer-Verlag.
Fukuda, Toshio et al., "A new method of master-slave type of teleoperation for a micro-manipulator system," IEEE Microrobots and Teleoperations Workshop, 1987, 5 pages, IEEE.
Funda J., et al., "An experimental user interface for an interactive surgical robot," In 1st International Symposium on Medical Robotics and Computer Assisted Surgery (MRCAS 94), 1994, pp. 196-203.
Funda J., et al., "Constrained Cartesian Motion Control for Teleoperated Surgical Robots," IEEE Transactions on Robotics and Automation, IEEE, Jun. 1996, vol. 12 (3), pp. 453-465.
Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.
Funda, Janez et al., "Control and evaluation of a 7-axis surgical robot for laparoscopy," IEEE Int. Conf. on Robotics and Automation, 1995, pp. 1477-1484, vol. 2, IEEE.
Funda, Janez et al., "Image-Guided Command and Control of a Surgical Robot," Proc. Medicine Meets Virtual Reality II, 1994, pp. 52-57.
Funda, Janez et al., "Optimal Motion Control for Teleoperated Surgical Robots," Intl. Symp. on Optical Tools for Manuf. & Adv Autom, Telemanipulator Technology and Space Telerobotics, 1993, pp. 211-222, vol. 2057, SPIE.
Furuta, Katsuhisa et al., "Master slave manipulator based on virtual internal model following control concept," IEEE Intl. Conference on Robotics and Automation, 1987, pp. 567-572, vol. 1, IEEE.

(56) References Cited

OTHER PUBLICATIONS

Ganssle J.G.,,A Guide to Debouncing, The Ganssle Group, Jun. 2008,26 pages.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol. 77.
Gelb, A., et al., Table of Contents for "Applied Optimal Estimation," The Analytic Science Corporation, MIT Press, Cambridge, Massachusetts, 1974, 4 pages.
Gennari, G. et al., "Probabilistic data association methods in visual tracking of groups," IEEE Conference on Computer Vision and Pattern Recognition, 2004, pp. 1-790-1-797, vol. 1—issue. 27, IEEE.
Gigot, Jean-Francois et al., "Laparoscopic Liver Resection for Malignant Liver Tumors Prelimary Results of a Multicenter European Study," Ann Surg, 2002, pp. 90-97, vol. 236—issue 1.
Gonzales, Adriana Vilchis et al., "A System for Robotic Tele-echography," Medical Image Computing and Computer-Assisted Intervention, 2001, pp. 326-334, vol. 2208, Springer.
Green, Philip, S. et al., "Mobile telepresence surgery," 2nd Annual Intl Symposium on Med. Robotics and Computer Assisted Surgery, Maryland Nov. 1995, pp. 97-103.
Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.
Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.
Hager G., et al., "The X Vision System: A Portable Substrate for Real Time Vision Applications," Computer Vision and Image Understanding, 1998, vol. 69 (1), pp. 23-37.
Hager, Gregory D., "A Modular System for Robust Positioning Using Feedback from Stereo Vision," IEEE Transactions on Robotics and Automation, Aug. 1997, vol. 13 (4), pp. 582-595.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.
Hager Gregory D. et al., "Multiple Kernel Tracking with SSD," Proceedings of the IEEE Conference on Computer Vision and Pattern Recognition (CVPR 2004), 2004, pp. 1-790-1-797, vol. 1—issue 27, IEEE.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.
Harris, S.J. et al., "A robotic procedure for transurethral resection of the prostate," Second Annual International Symposium on Medical Robotics and Computer Assisted Surgery, 1995, pp. 264-271.
Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.
Herline A.J., et al., "Image-Guided Surgery: Preliminary Feasibility Studies of Frameless Stereotactic Liver Surgery," Archives of Surgery, 1999, vol. 134 (6), pp. 644-650.
Herline, Alan J. et al., "Surface Registration for Use in Interactive," Image-Guided Liver Surgery, Computer Aided Surgery, 2000, pp. 11-17, vol. 5—No. 2.
Herman, Barry C., et al., "Telerobotic surgery creates opportunity for augmented reality surgery," Abstract No. T1F2, Telemedicine Journal and E-Health, vol. 11, Issue 2, p. 203, Apr. 2005.
Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.
Herper Matthew, "Watch a $1.5 Million Surgical Robot Play a Board Game," Forbes. Apr. 12, 2011. 2 pages, Online [Available: http://www.forbes.com/sites/matthewherper/2011/04/12/watch-a-1-5-million-surgical-robot-play-a-board-game/#587224f011f5] Accessed Jun. 7, 2016.
Hespanha J.P., et al., "What Tasks Can Be Performed with an Uncalibrated Stereo Vision System," International Journal of Computer Vision, Nov. 1999, vol. 35 (1), 33 pages.
Hill J.W., et al., "Telepresence surgery demonstration system," IEEE International Conference on Robotics and Automation, 1994, vol. 3, pp. 2302-2307.
Ho, S. C. et al., "Robot Assisted Knee Surgery," IEEE Engineering in Medicine and Biology Magazine, 1995, pp. 292-300, vol. 14—Iss. 3, IEEE.
Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.
Horn, Berthold K.P., "Closed-form solution of absolute orientation using unit quaternions," Journal of the Optical Society of America A, vol. 4, No. 4, pp. 629-642, Apr. 1987.
Hunter, Ian W. et al., "A teleoperated microsurgical robot and associated virtual environment for eye surgery," Presence: Teleoperators and Virtual Environments, 1993, pp. 265-280, vol. 2—No. 4, MIT Press.
Hunter, Ian W. et al., "Ophthalmic microsurgical robot and associated virtual environment," Comput. Biol. Med, 1995, vol. 25, Issue 2, pp. 173-182, Pergamon.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Hutchinson, Seth et al., "A Tutorial Visual Servo Control," IEEE Transactions on Robotics and Automation, 1996, pp. 651-670, vol. 12 issue.5, IEEE.
IEEE Systems and Software Engineering—Recommended Practice for Architectural Description of Software-Intensive Systems, IEEE Std 1471-2000, 34 pages, First Edition, Jul. 15, 2007.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Search Report and Written Opinion for Application No. PCT/US2012/064379, mailed on Mar. 29, 2013, 12 pages.
International Search Report and Written Opinion for Application No. PCT/US2012/064400, mailed on Mar. 27, 2013, 10 pages.
Intuitive Surgical, Inc., "Intuitive Surgical daVinci API v5.0 Reference Manual," generated Jul. 17, 2006, 149 pages.
Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.
Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.
Johns Hopkins University and Intuitive Surgical, Inc., "System Requirements for the Surgical Assistant Workstation," Rev. 2, Jan. 29, 2007, 17 pages.
Jones D.B. et al., Chapter 25, "Next-Generation 3D Videosystems may Improve Laparoscopic Task Performance," Interactive Technology and the New Paradigm for Healthcare, 1995, pp. 152-160.
Joskowicz L., et al., "Computers in Imaging and Guided Surgery," Computing in Science and Engineering, 2001, vol. 3 (5), pp. 65-72.
Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.

(56) References Cited

OTHER PUBLICATIONS

Kane, Robert A., "Intraoperative Ultrasonography, History, Current State of the Art, and Future Directions," J Ultrasound Med, 2004, pp. 1407-1420, vol. 23.
Kaplan, Irving, "Minimizing Rectal and Urinary Complications in Prostate Brachytherapy," Journal of Endourology, 2000, pp. 381-383.
Kapoor A., et al., "Simple Biomanipulation Tasks with "Steady Hand" Cooperative Manipulator," Lecture Notes in Computer Science, 2003, vol. 2878, pp. 141-148.
Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.
Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.
Kapoor, Ankur et al., "Suturing in Confined Spaces: Constrained Motion Control of a Hybrid 8-DOF Robot," Proceedings, 12th International Conference on Advanced Robotics, 2005, pp. 452-459.
Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.
Kato H., et al., "The Effects of Spatial Cues in Augmented Reality Video Conferencing," Hiroshima City University, Aug. 2001, 4 pages.
Kato H., et al. "Virtual Object Manipulation on a Table-Top AR Environment," Hiroshima City University, 2000, 9 pages.
Kavoussi L.R., "Laparoscopic Donor Neptarectomy," Kidney International, 2000, vol. 57, pp. 2175-2186.
Kazanzides P., et al., "Force Sensing and Control for a Surgical Robot," Int. Conference on Robotics and Automation, May 1992, vol. 1, pp. 612-617.
Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.
Kazerooni, H., "Human Extenders," ASME J. Dynamic Systems, Measurements and Control, 1993, pp. 281-290, vol. 115 No. 2(B).
Kazerooni, H., "Design and analysis of the statically balanced direct-drive robot manipulator," Robotics and Computer-Integrated Manufacturing, 1989, pp. 287-293, vol. 6, Issue 4.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kilmer, R. D. et al., "Watchdog safety computer design and implementation," RI/SME Robots 8 Conference, Jun. 1984, pp. 101-117.
Kim, Won S. et al., "Active compliance and damping in telemanipulator control," Jet Propulsion Laboratory New technology Report, 1991, pp. 1-14a, vol. 15—Issue 4, JPL & NASA Case No. NP0-1796917466, Item 40.
Kitagawa, Masaya et al., "Effect of Sensory Substitution on Suture Manipulation Forces for Surgical Teleoperation," 12th Annual Medicine Meets Virtual Reality Conference, 2005, 8 pages.
Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.
Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.
Komada, Satoshi et al., "Bilateral robot hand based on estimated force feedback," IEEE Proceedings IECON 87 Cambridge MA, Nov. 3-6, 1987, pp. 602-607, vol. 2, IEEE.
Kon, Ryan et al., "An open-source ultrasound calibration toolkit," Medical Imaging Ultrasonic Imaging and Signal Processing, 2005, pp. 516-523, vol. 5750, SPIE.
Korein James U. et al., "A Configurable System for Automation Programming and Control," IEEE Conf. on Robotics and Automation. San Francisco, 1986, pp. 1871-1877, vol. 3, IEEE.
Kosugi, Yukio et al., "An articulated neurosurgical navigation system using MRI and CT Images," IEEE Transactions on Biomedical Engineering, 1988, pp. 147-152, vol. 35—Issue 2, IEEE.
Kragic D. et al., "Human-Machine Collaborative Systems for Microsurgical Applications," International Symposium on Robotics Research, 2005, pp. 731-741, vol. 24—Issue 9, Sage Publications.
Kruchten, Philippe B., "The 4+1 View Model of Architecture," IEEE Software, vol. 12, Issue 6, pp. 42-50, Nov. 1995.
Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention—Part , Lecture Notes in Computer Science, 2002, pp. 9-16, vol. 2488, Springer Verlag.
Kumar R., "An Augmented Steady Hand System for Precise Micromanipulation," PhD thesis in Computer Science, The Johns Hopkins University, Baltimore, Apr. 2001, 118 pages.
Kumar, R., et al., "An Augmentation System for Fine Manipulation," Proceedings of the Third International Conference on Medical Image Computing and Computer-Assisted Intervention, Lecture Notes in Computer Science, 2000, vol. 1935, pp. 957-965.
Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes In Computer Science, 2001, pp. 1417-1418, vol. 2208, Springer Verlang.
Kumar, Rajesh et al., "Experiments with a Steady Hand Robot in Constrained Compliant Motion and Path Following", 1999, pp. 92-97, IEEE.
Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.
Kumar, Rajesh et al., "Preliminary experiments in robot/human microinjection," IEEE/RSJ International Conference on Intelligent Robots and Systems, 2003, pp. 3186-3191, vol. 3, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Lacroute, P., "The VolPack Volume Rendering Library," 1995, information downloaded from https://graphics.stanford.edu/software/volpack/ , 4 pages.
Lacroute, Philippe G., "Fast Volume Rendering Using a Shear-Warp Factorization of the Viewing Transformation PhD Thesis," Computer Science, Stanford, California, 1995, 236 Pages.
Lang, Samuel J., Xvision 2—A Framework for Dynamic Vision. Masters Thesis, Computer Science, Johns Hopkins University, Baltimore, 2001, pp. 1-49.
Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.
Lau, W.W., et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, vol. 2, pp. 494-501.
Lavonius, Maija I. et al., "Staging of Gastric Cancer: A Study with Spiral Computed Tomography, Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.

(56) References Cited

OTHER PUBLICATIONS

Lawson, Charles L. et al., "Linear least squares with linear inequality constraints Solving Least Squares Problems," 1974, pp. 158-173, Prentice Hall Inc.

Lazarevic, Zoran, "Feasibility of a Stewart Platform with Fixed Actuators as a Platform for CABG Surgery Device," 1997, 45 pages, Master's Thesis Columbia University Department of Bioengineering.

Lee Jr, F.T., et al., "CT-monitored Percutaneous Cryoablation in a Pig Liver Model: Pilot Study," Radiology, 1999, vol. 211 (3), pp. 687-692.

Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.

Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.

Levoy, Marc, "Display of Surfaces from Volume Data," IEEE Computer Graphics and Applications, 1988, pp. 29-37, vol. 8—Iss. 3, IEEE.

Li, M., "Intelligent Robotic Surgical Assistance for Sinus Surgery," Ph.D. Dissertation, Johns Hopkins University, Baltimore, Aug. 2005, 246 pages.

Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.

Li, Ming and Russell H. Taylor, "Performance of surgical robots with automatically generated spatial virtual fixtures," IEEE International Conference on Robotics and Automation, Barcelona, Spain, Apr. 2005, pp. 217-222.

Li, Ming et al., "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures," IEEE, HAPTICS 2003, 11th Symposium on Haptic Interfaces for Virtual Environment and Teleoperator Systems, Mar. 22-23, 2003, pp. 125-131, IEEE.

Lievin et al., "Stereoscopic Augmented Reality System for Computer Assisted Surgery," CARS 2001, Jun. 27-30, 2001, 5 pages.

Loser, Michael H. et al., "A New Robotic System for Visually Controlled Percutaneous Interventions under CT Fluoroscopy," Medical Image Computing and Computer-Assisted Interventions, Lecture Notes in Computer Science, 2000, pp. 887-896, vol. 1935, Springer Verlag.

Loser, Michael H. et al., "Visual servoing for automatic and uncalibrated percutaneous procedures," SPIE Medical Imaging, 2000, pp. 270-281, vol. 3976, SPIE.

Lunwei Z., et al., "FBG Sensor Devices for Spatial Shape Detection of Intelligent Colonoscope," IEEE International Conference on Robotics and Automation, Apr. 2004, New Orleans, Louisiana, pp. 835-840.

Madhani A.J., "Design of Teleoperated Surgical Instruments for Minimally Invasive Surgery," Feb. 1998, 251 pages.

Maehara, S. et al., "Laparoscopy-Assisted Hepatectomy Using the Endoclose," Surgical Endoscopy, 2002, vol. 16 (9), pp. 1363-1364.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. by Lippincott Williams & Wilkins, Philadelphia, 2004, pp. 26-31.

Masamune K., et al., "Development of a MRI Compatible Needle Insertion Manipulator for Stereotactic Neurosurgery," Journal of Image Guided Surgery, 1995, vol. 1, pp. 242-248.

Masamune K., et al., "System for Robotically Assisted Percutaneous Procedures With Computed Tomography Guidance," Journal of Computer-Assisted Surgery, 2001, vol. 6 (6), pp. 370-383.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken H. et al., "A Newly Developed Stereotactic Robot with Detachable Drive for Neurosurgery," 1st International Conference on Medical Image Computing and Computer-Assisted Intervention—MICCAI, Cambridge, Massachusetts; Springer, Oct. 11-13, 1998, pp. 215-222, vol. 1496.

Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, 7 pages.

Mayer, Hermann et al., "Skill Transfer and Learning by Demonstration in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes In Computer Science, 2001, pp. 343-350, vol. 2208, Springer-Verlag.

Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.

Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.

Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.

Michael B. Cohn's Home Page, http://www.bsac.eecs.berkeley.edu/users/michaelc/, downloaded Nov. 1, 1996, p. 1; UC Berkeley/ Endorobotics Corporation Surgical Robotics Project Job Openings, http:/www.bsac.eecs.berkeley.edu/users/michaelc/jobs.html, downloaded Nov. 1, 1996, p. 1; and Medical Robotics, http://robotics.eecs.berkeley.edu/~mcenk/medical/, downloaded Nov. 1, 1996, pp. 1-8.

Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.

Mitsuishi M., et al., "A tele-micro-surgery system with co-located view and operation points and a rotational-force-feedback-free

(56) References Cited

OTHER PUBLICATIONS master manipulator," 2nd Annual Intl. Symposium on Medical robotics and Computer Assisted Surgery Baltimore Maryland, Nov. 4-7, 1995, pp. 111-118.
Mitsuishi, Mamoru et al., "Remote Ultrasound Diagnostic System," Conf. on Robotics and Automation, 2001, pp. 1567-1574, vol. 2, IEEE.
Mourgues, Fabien et al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes In Computer Science, 2002, pp. 25-34, vol. 2488, Springer-Verlag.
Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.
Nakakura, Eric K. et al., "Hepatocellular Carcinoma: Current Management Recommendations," Advances on Oncology, 2000, pp. 12-18, vol. 16—No. 2.
Neisius B. et al., "Robotic manipulator for endoscopic handling of surgical effectors and cameras," 1st Intl. Symposium on Medical Robotics and Computer Assisted Surgery, 1994, pp. 169-175, vol. 2.
Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.
Nelson, Thomas, R. et al., "Three-dimensional ultrasound imaging," Ultrasound in Medicine & Biology, 1998, pp. 1243-1270, vol. 24—No. 9, Elsevier.
Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.
Novotny Paul M. et al., "Tool Localization in 3D Ultrasound Images," Medical Image Computing and Computer-Assisted Intervention, 2003, pp. 969-970, vol. 2879, Springer.
Office Action dated Nov. 29, 2019 for U.S. Appl. No. 15/638,172, filed Jun. 29, 2017, 11 pages.
Office Action mailed May 1, 2012 for Japanese Application No. 20090518470 filed Jun. 22, 2007, 7 pages.
Office Action mailed Sep. 3, 2014 for Chinese Application No. 2010823529 filed Mar. 26, 2010, 8 pages.
Office Action mailed Jan. 4, 2016 for European Application No. 10717330.4 filed Mar. 26, 2010, 8 pages.
Office Action mailed Jul. 6, 2016 for Japanese Application No. 2015202607 filed Oct. 14, 2015, 7 pages.
Office Action mailed May 9, 2016 for Korean Application No. 10-2011-7025321 filed Oct. 26, 2011, 18 pages.
Office Action mailed Feb. 12, 2015 for Chinese Application No. 2010823529 filed Mar. 26, 2010, 6 pages.
Office Action mailed Jun. 12, 2015 for Japanese Application No. 20130186992 filed Sep. 10, 2013, 8 pages.
Office Action mailed Jul. 14, 2013 for Japanese Application No. 20120503535 filed Mar. 26, 2010, 3 pages.
Office Action mailed Dec. 16, 2016 for Japanese Application No. 2015242062 filed Oct. 14, 2015, 13 pages.
Office Action mailed Jan. 21, 2014 for Chinese Application No. 2010823529 filed Mar. 26, 2010, 44 pages.
Office Action mailed Mar. 24, 2014 for Japanese Application No. 20120503535 filed Mar. 26, 2010, 13 pages.
Office Action mailed Jan. 26, 2015 for Japanese Application No. 20130186992 filed Sep. 10, 2013, 9 pages.
Office Action mailed Nov. 29, 2013 for Japanese Application No. 20120503535 filed Mar. 26, 2010, 11 pages.
Office Action mailed Oct. 24, 2019 for Korean Application No. 1020197022941 filed May 11, 2011, 14 pages.
Ohbuchi R., et al., "Incremental Volume Reconstruction and Rendering for 3D Ultrasound Imaging," The International Society of Optical Engineering, 1992, vol. 1808, pp. 312-323.
Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.
Patriciu A., et al., "Motion-based Robotic Instrument Targeting under C-Arm Fluoroscopy," Medical Image Computing and Computer-Assisted Interventions, 2000, vol. 1935, pp. 988-998.
Paul, Howard A. et al., "Development of a Surgical Robot for Cementless Total Hip Arthroplasty," Clinical Orthopaedics, Dec. 1992, pp. 57-66, vol. 285.
Payandeh S., et al., "On Application of Virtual Fixtures as an Aid for Telemanipulation and Training," Proceedings 10th Symposium on Haptic Interfaces for Virtual Environment and Teleoperator Systems (HAPTICS), Mar. 2002, pp. 18-23.
PCT/US07/71850 International Search Report and Written Opinion of the International Searching Authority, mailed Feb. 13, 2008, 9 pages.
PCT/US09/46234 International Search Report and Written Opinion of the International Searching Authority, mailed Sep. 9, 2009, 13 pages.
PCT/US09/56078 International Search Report and Written Opinion of the International Searching Authority, mailed Jan. 20, 2010, 12 pages.
PCT/US10/28886 International Search Report and Written Opinion of the International Searching Authority, mailed Jul. 6, 2010, 11 pages.
PCT/US10/28897 International Search Report and Written Opinion of the International Searching Authority, mailed Jul. 19, 2010, 16 pages.
PCT/US10/38246 International Search Report and Written Opinion of the International Searching Authority, mailed Sep. 14, 2010, 17 pages.
PCT/US2011/036109 International Search Report and Written Opinion of the International Searching Authority, mailed Oct. 19, 2011, 16 pages.
PCT/US2011/036109 Invitation to Pay Additional Fees and Partial International Search Report, mailed Aug. 18, 2011, 5 pages.
Podnos Y.D., et al., "Laparoscopic Ultrasound with Radiofrequency Ablation in Cirrhotic Patients with Hepatocellular Carcinoma: Technique and Technical Considerations," American Surgeon, Dec. 2001, vol. 67 (12), pp. 1181-1184.
Pose—definition from Merriam Webster Dictionary, 4 pages, [online], [retrieved on Apr. 3, 2015]. Retrieved from the Internet: URL: http://www.merriam-webster.com/dictonary/pose.
Posture—definition from Merriam Webster Dictionary, 4 pages, [online], [retrieved on Apr. 3, 2015]. Retrieved from the Internet: URL: http://www.merriam-webster.com/dictonary/posture.
Poulose B.K., et al., "Human vs Robotic Organ Retraction During Laparoscopic Nissen Fundoplication," Surgical Endoscopy, 1999, vol. 13, pp. 461-465.
Prager Richard et al., "Practical segmentation of 3D ultrasound," In Proceedings of Medical Image Understanding and Analysis, 1999, pp. 161-164.
Prager Richard et al., "Rapid Calibration for 3D Freehand Ultrasound," Ultrasound in Medicine and Biology, 1998, pp. 855-869, vol. 24—No. 6, Elsevier.
Prasad, Srinivas K. et al., "A minimally invasive approach to pelvic osteolysis," 2002, in Proc. Computer-Assisted Orthopaedic Surgery (CAOS), pp. 349-350.
Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI, Lecture Notes in Computer Science, 2003, pp. 279-286, vol. I, Springer.
Pre-Appeal Examination Report, mailed Sep. 3, 2014 for Japanese Application No. JP20120503535 filed Mar. 26, 2010, 7 pages.
Preising B., et al., "A Literature Review: Robots in Medicine," IEEE Engineering in Medicine and Biology, Jun. 1991, vol. 10(2), pp. 13-22.
Ramey, N. A., "Stereo-Based Direct Surface Tracking with Deformable Parametric Models," Thesis submitted to The Johns Hopkins University, Maryland, Apr. 2003, 104 pages.

(56) References Cited

OTHER PUBLICATIONS

Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.
Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.
Ratner, Lloyd E. et al., "Laparoscopic live donor nephrectomy removes disincentives to live donation," Transplantation, 1997, pp. 3402-3403, vol. 29—Issue 8, Elsevier.
Ratner, Lloyd E. et al., "Laparoscopic live donor nephrectomy," Transplantation, 1995, pp. 1047-1049.
Rau, Beate, M. eta al., "Is There Additional Information From Laparoscopic Ultrasound in Tumor Staging", Digestive Surgery, 2002, pp. 479-483, vol. 19—No. 6.
Rockall, Timothy A., "The da Vinci Telerobotic Surgical System," Chapter 8 in Primer of Robotic & Telerobotic Surgery, Eds. Garth H. Ballantyne et al., Pub. by Lippincott Williams & Wilkins, Philadelphia, 2004, pp. 57-60.
Rohling, Robert et al., "Three-dimensional spatial compounding of ultrasound images," Medical Image Analysis, 1996, pp. 177-193, vol. 1—No. 3, Oxford University Press.
Rohling, Robert N. et al., "Radial basis function interpolation for 3-d ultrasound," CUED/F-INFENG/TR 327, Cambridge University, Jul. 1998, 28 Pages.
Rosen J., et al., "The BlueDRAGON—A System for Measuring the Kinematics and the Dynamics of Minimally Invasive Surgical Tools In-Vivo," Proceedings of the 2002 IEEE International Conference on Robotics & Automation, 2002, pp. 1876-1881.
Rosenberg, Louis B., "Human interface hardware for virtual laparoscopic surgery," Proceedings of the Interactive Technology and the New Paradigm for Healthcare, 1995, pp. 322-325, Amsterdam: IOS Press.
Rosenberg, Louis B., "Virtual Fixtures: Perceptual Tools for Telerobotic Manipulation," IEEE Virtual Reality International Symposium, 1993, pp. 76-82, IEEE.
Rothbaum Daniel L. et al., "Robot-assisted stapedotomy: micropick fenestration of the stapes footplate," Otolaryngology—Head and NeckSurgery, 2002, pp. 417-426, vol. 127.
Rothbaum Daniel L. et al., "Task Performance in stapedotomy: Comparison between surgeons of different experience levels," Otolaryngology—Head and Neck Surgery, 2003, pp. 71-77, vol. 128—No. 1.
Roy, Jaydeep, "Advances in the design, analysis and control of force controlled robots," Master's Thesis, Mechanical Engineering, Johns Hopkins University, Baltimore, 2001, 210 Pages.
Sakas, Georgios et al., "Extracting surfaces from fuzzy 3D-Ultrasound data," Proceedings of the 22nd annual conference on Computer graphics and interactive techniques, 1995, pp. 465-474.
Salcudean, Septimiu E. et al., "A Robot System for Medical Ultrasound," 9th International Symposium of Robotics Research (ISRR'99), 1999, pp. 195-202.
Santambrogio, R. et al., "Ultrasound-Guided Interventional Procedures of the Liver During Laparoscopy: Technical Considerations," Surg Endosc, 2002, pp. 349-354, Springer-Verlag.
Sastry S., "MilliRobotics in Minimally Invasive Telesurgery," Retrieved from Internet [URL: http://robotics.eecs.berkeley.edu ] 1995, 3 pages.
Sastry, Shankar, http://robotics.eecs.berkeley.edu, Nov. 1, 1995, Total 8 pages.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.
Schorr, O., et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, vol. 1935, pp. 979-987.
Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.
Schweikard, Achim et al., "Motion Planning in Stereotaxic Radiosurgery," IEEE Transactions on Robotics and Automation, 1993, pp. 909-916, vol. 1, IEEE.
Scott D.J., et al., "Accuracy and Effectiveness of Laparoscopic vs Open Hepatic Radiofrequency Ablation," Surgical Endoscopy, Feb. 2001, vol. 15 (2), pp. 135-140.
Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.
Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.
Solomon S.B., et al., "Robotically Driven Interventions: A Method of Using CT Fluoroscopy without Radiation Exposure to the Physician," Radiology, 2002, vol. 225, pp. 277-282.
Solus-3D Ultrasound Project in Obstetrics and Gynaecology, University of Cambridge, http://mi.eng.cam.ac.uk/research/projects/Solus/, downloaded Jul. 5, 2007, 4 pages.
Sommer, Graham et al., "Liver tumors: utility of characterization at dual frequency US," Radiology, 1999, pp. 629-636, vol. 211—No. 3.
Steele, Micah R. et al., "Shared control between human and machine: using a haptic steering wheel to aid in land vehicle guidance," Human Factors and Ergonomics Society 45th Annual Meeting, Minneapolis, Minnesota, 2001, pp. 1671-1675.
Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.
Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.
Stetten, George D. et al., "Overlaying Ultrasound Images on Direct Vision," Journal of Ultrasound in Medicine, 2001, pp. 235-240, vol. 20—No. 3.
Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.
Stoianovici D., et al., "Robotic Telemanipulation for Percutaneous Renal Access," in 16th World Congress On Endourology, New York City, Sep. 3-6, 1998, Poster Session 17-5, p. S201.
Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.
Stoianovici, Dan et al., "Robotic for Precise Percutaneous Needle Insertion," In Thirteenth Annual Meeting of the Society for Urology and Engineering. San Diego, May 1998, pp. 4.
Stoll, Jeff, "Ultrasound-based servoing of manipulators for telesurgery," Telemanipulator and Telepresence Technologies VIII Conference, 2001, pp. 78-85, SPIE.
Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.
Suramo, I. et al., "Cranio-caudal movements of the liver, pancreas and kidneys in respiration," Acta Radiologica: Diagnosis, 1984, pp. 129-131, vol. 25, Radiological Societies.

(56) References Cited

OTHER PUBLICATIONS

Susil, Robert, C. et al., "A Single Image Registration Method for CT Guided Interventions," 2nd International Symposium on Medical Image Computing and Computer-Assisted Interventions (MICCAI' 99), Lecture Notes in Computer Science, 1999, pp. 798-808, vol. 1679, Springer-Verlag.
Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.
Taubes, Gary et al., "Surgery in Cyberspace," Discover magazine, Dec. 1994, vol. 15, issue 12, pp. 85-92.
Tavakoli, M., et al., A Force Reflective Master-Slave System for Minimally Invasive Surgery, Proc. IEEE/RSJ International Conference on Intelligent Robots and Systems, 2003, pp. 3077-3082, vol. 4, IEEE.
Taylor R., et al., "A Telerobotic System for Augmentation of Endoscopic Surgery," in IEEE Conference on Engineering in Medicine and Biology, 1992, vol. 14, pp. 1054-1056.
Taylor R.H., et al., "A Computational Architecture for Programmable Automation Research," Intelligent Robots and Computer Vision, 1986, vol. 726, pp. 438-440.
Taylor, R.H., et al., "A General Purpose Control Architecture for Programmable Automation Research," Proceedings of the Third International Symposium on Robotics, 1986, pp. 165-173, MIT Press.
Taylor R.H. et al., "Medical Robotics and Computer-Integrated Surgery," Chapter 52 in Springer Handbook of Robotics, Springer, 2008, pp. 1199-1222.
Taylor R.H., et al., Table of Contents, "Computer-Integrated Surgery," Technology and Clinical Applications, The MIT Press, Cambridge, MA, 1996, 8 pages.
Taylor, R.H., "Medical Robotics and Computer-Integrated Surgery," Handbook of Industrial Robotics, Second Edition, 1999, pp. 1213-1227, Chapter 65, John Wiley & Sons.
Taylor, Russell H., "A Perspective on Medical Robotics," Proceedings of the IEEE, vol. 94, No. 9, Sep. 2006, pp. 1652-1664.
Taylor, Russell H. "An Image-directed Robotic System for Precise Orthopaedic Surgery," IEEE Transactions on Robotics mid Automation, 1994, pp. 261-275, vol. 10—No. 3, IEEE.
Taylor, Russell H. and Christopher Hasser, "Development of a Surgical Assistant Workstation for Teleoperated Surgical Robots," NSF Proposal No. 0646678, Aug. 2006, 16 pages.
Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.
Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.
Taylor, Russell, H. et al., "A Steady-Hand Robotic System for Microsurgical Augmentation," International Journal of Robotics Research, 1999, pp. 1201-1210, vol. 18—No. 12, Springer-Verlag.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell, H. et al., "AML A Manufacturing Language," The International Journal of Robotics Research, 1982, pp. 19-41, vol. 1—No. 3, SAGE Publications.
Taylor, Russell H. et al., "An Image-directed Robotic System for Hip Replacement Surgery," J. Robotics Society of Japan, 1990, pp. 615-620, vol. 8—issue 5.
Taylor, Russell, H. et al., "An Integrated Robot Systems Architecture," Proceedings of the IEEE, 1983, pp. 842-856, vol. 71—Issue 7, IEEE.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.
Taylor, Russell H. et al., "Medical Robotics in Computer-Integrated Surgery," IEEE Transactions on Robotics md Automation, 2003, pp. 765-781, vol. 19—No. 5, IEEE.
Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.
Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell, H. et al., "The Architecture of an Integrated Robot System," First Int. Conf. on Advanced Robotics (ICAR)., 1983, pp. 389-398.
Taylor, Russell H. "Medical Robots," in Computer and Robotic Assisted Knee and Hip Surgery, 2004, pp. 54-59, Oxford Press.
Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.
Taylor, Russell H. "The Planning and Execution of Straight Line Manipulator Trajectories," IBM Journal of Research and Development, 1979, pp. 424-436, vol. 23—Issue 4.
Taylor, Russell H., "Ultrasound Assistant for a Laparoscopic Surgical Robot," NIH STTR Phase II Proposal R42-RR019159, revised May 2001, 54 pages.
Taylor, Russell H., Videotape: "Computer Assisted Surgery at IBM T. J. Watson Research Center," 22 minutes 10 seconds, 1994 and 1995.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-572, vol. 60—No. 4, Elsevier.
Thring, M.W., "Robots and Telechirs: Manipulators with Memory; Remote Manipulators; Machine Limbs for the Handicapped," Ellis Horwood Limited, England, 1983, 79 pages, including Table of Contents, Preface, Chap. 5 (pp. 108-131), Chap. 7 (pp. 194-195, 235), Chap. 8 (pp. 236-278), Chap. 9 (p. 279).
Toon, John, "Virtual Reality for Eye Surgery," Georgia Tech Research News, 1993, 4 Pages.
Toyama, Kentaro et al., "Incremental Focus of Attention for Robust Vision-based Tracking," International Journal of Computer Vision, 1999, pp. 45-63, vol. 35—No. 1, Kluwer Academic Publishers.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trivedi, Mohan M. et al., "Developing telerobotic systems using virtual reality concepts," 1993 IEEE/RSJ International Conference on Intelligent Robots and systems, 1993, pp. 352-359, vol. 1, IEEE.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery, Lecture Notes in Computer Science, 1997, pp. 727-736, vol. 1205, Springer-Verlag.
Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.
U.S. Appl. No. 11/583,963 Non-Final Office Action mailed Jul. 9, 2009, 40 pages.

(56) References Cited

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Vibet, C., "Properties of Master-Slave Robots," Motor-con, MOTORCON'87, Hannover, Apr. 1987, pp. 309-316.

Vilchis, Adriana et al., "A New Robot Architecture for Tele-Echography," IEEE Trans. Robotics & Automation, pp. 922-926, 2003, vol. 19—No. 5, IEEE.

Viswanathan, Anand et al., "Immediate Ultrasound Calibration with Three Poses and Minimal Image Processing," MICCAI, 2004, pp. 446-454, vol. 2, Springer-Verlag.

Webster R.J. et al., "Nonholonomic Modeling of Needle Steering," The International Journal of Robotics Research, 2006, vol. 25 (5-6), pp. 509-525.

Webster Robert J. et al., "Design Considerations for Robotic Needle Steering," International Conference on Robotics and Automation, 2005, pp. 3588-3594, IEEE.

Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

Wei, Zhouping et al "Robot-assisted 3D-TRUS guided prostate brachytherapy: system integration and validation," Medical Physics, 2004, pp. 539-548, vol. 31—No. 3.

Wengert, C., "Camera Calibration Toolbox for Matlab," http://www.vision.caltech.edu/bouguetj/calib_doc/, downloaded Oct. 24, 2006, 9 pages.

Wilhelm, Dirk et al., "Electromagnetically Navigated Laparoscopic Ultrasound," Surg. Technol. Int, 2003, pp. 50-54, vol. 11.

Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.

Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.

Xu, Sheng et al., "3D Motion Tracking of Pulmonary Lesions Using CT Fluoroscopy Images for Robotically Assisted Lung Biopsy," Proc. SPIE. 5367, Medical Imaging 2004: Visualization, Image-Guided Procedures, and Display, 394. (May 5, 2004), pp. 394-402.

Yamagata H., et al., "Development of a New Display Method for Compound 3D Ultrasound Images: Fusion 3D Images From B-mode and 3D Doppler Images," 1999, vol. 70, pp. 43-46.

Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.

Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.

Yao, Jianhua et al., "Deformable registration between a statistical born density atlas and X-ray images," Second International Conference on Computer Assisted Orthopaedic Surgery, 2002, pp. 168-169.

Zacherl, Johannes et al., "Current value of intraoperative sonography during surgery for hepatic neoplasms," World J Surg, 2002, pp. 550-554, vol. 26—No. 5.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

Zhang, Z., "A Flexible New Technique for Camera Calibration," Technical report MSR-TR-98-71, Microsoft Research, Microsoft Corporation, Redmond, WA, Dec. 1998, pp. 1-21.

* cited by examiner

SYNTHETIC REPRESENTATION OF A SURGICAL ROBOT

CROSS-REFERENCE TO RELATED APPLICATIONS

This application is a continuation of U.S. patent application Ser. No. 16/932,373 (filed Jul. 17, 2020) which is a continuation of U.S. patent application Ser. No. 16/161,204 (filed Oct. 16, 2018) which is a continuation of U.S. patent application Ser. No. 15/629,533 (filed Jun. 21, 2017) which is a division of U.S. patent application Ser. No. 12/415,354 (filed Mar. 31, 2009) which is a continuation in part of U.S. patent application Ser. No. 11/478,531 (filed Jun. 29, 2006) and a continuation in part of U.S. patent application Ser. No. 12/163,087 (filed Jun. 27, 2008), all of which are incorporated herein by reference in their entireties.

BACKGROUND

Minimally invasive surgeries performed by robotic surgical systems are known and commonly used in remote or in other environments where it is advantageous for a human not to perform surgery. One example of such a telerobotic surgical system is the minimally invasive robotic surgery system described in commonly owned U.S. Pat. No. 7,155,315. The da Vinci® Surgical Systems manufactured by Intuitive Surgical, Inc. of Sunnyvale, California are illustrative implementations of minimally invasive robotic surgical systems (e.g., teleoperated; telesurgical).

A common form of minimally invasive surgery is endoscopy. Endoscopic surgical instruments in minimally invasive medical techniques generally include an endoscope for viewing the surgical field, and working tools that include end effectors. Typical surgical end effectors include clamps, graspers, scissors, staplers, or needle holders, as examples. The working tools are similar to those used in conventional (open) surgery, except that the end effector of each tool is supported on the end of, for example, an approximately 12-inch-long extension tube.

To manipulate end effectors, a human operator, typically a surgeon, manipulates or otherwise commands a locally-provided master manipulator. Commands from the master manipulator are translated as appropriate and sent to a remotely-deployed slave manipulator. The slave manipulator then manipulates the end effectors according to the operator's commands.

Force feedback may be included in minimally invasive robotic surgical systems. To provide such feedback, the remote slave manipulators typically provide force information to the master manipulator, and that force information is utilized to provide force feedback to the surgeon so that the surgeon is given the perception of feeling forces acting on a manipulator. In some force feedback implementations, haptic feedback may provide an artificial feel to the surgeon of tissue reactive forces on a working tool and its end effector.

Often, the master controls, which are typically located at a surgeon console, will include a clutch or other device for releasing one of the work tools at the patient site. This feature may be used, for example, in a system where there are more than two working tools. In such a system, the surgeon may release control of one working tool by one master and establish control over another working tool with that master.

The surgeon typically views an image of only the distal ends of the working tools that are within the endoscope's field of view. The surgeon cannot see portions of a tool, or an entire tool, that is outside the field of view. Accordingly, the surgeon cannot see if two or more tools are interfering with each other outside the field of view. Further, since the endoscope may be manipulated to be at various positions and orientations with reference to a surgical site and to the surgeon's body frame of reference, the surgeon may become confused about the general location of the tools. Consequently, the surgeon may not understand how to best move the master manipulators to avoid an inter-tool interference or to reorient one or more tools with reference to the surgical site.

SUMMARY

The following presents a simplified summary of some aspects and embodiments of the invention in order to provide a basic understanding of the invention. This summary is not an extensive overview of the invention. It is not intended to identify key/critical elements of the invention or to delineate the scope of the invention. Its sole purpose is to present some aspects and embodiments of the invention in a simplified form as a prelude to the more detailed description that is presented later.

In an embodiment, a robotic surgical system is provided. The system includes a robot including a linkage supporting at least one tool for performing surgery on a patient; a kinematic component coupled to the robot so as to obtain joint state information from the linkage; a display; and a first component coupling the display with the kinematic component so as to display a synthetic representation of the robot including a graphical representation of at least a portion of the linkage based upon linkage structure data regarding the linkage; and the joint state information.

In another embodiment, a robotic surgical system is provided. The system includes a robot including an image capture device having a field of view and a linkage supporting at least one tool for performing surgery on a patient; a kinematic component coupled to the linkage so as to obtain joint states information regarding the linkage; data regarding structure of the first linkage and said at least one tool; and a collision detection component coupled to the data and to the kinematic component so as to generate a warning.

In still another embodiment, a method of controlling a position of a tool in a robotic system is provided. The method includes displaying a first image on a display, the first image comprising a video feed of a tool or linkage of a robot within a field of view; displaying a second image on the display, the second image representing a three dimensional model of the tool or linkage, with the second image of the three dimensional model aligned with first image of the tool or linkage; and moving an input device with reference to the first and second images on the display so as to control movement of the tool or linkage.

In yet still another embodiment, a method of providing a range of motion of a tool of a robotic system is provided. The method includes displaying a first image representing a position of the tool; and superimposing on the first image a second image representing a limit of motion of the tool.

In yet another embodiment, a robotic system is provided. The method includes maintaining information about a position of a tool of a robotic system; and generating a signal as a result of the tool being within a threshold distance from a limit of motion of the tool.

In another embodiment, a robotic surgical system is provided. The system includes a robot including a linkage supporting at least one tool for performing surgery on a patient; an image capture device having a field of view encompassing the tool; a kinematic component coupled to the robot so as to obtain joint state information from the linkage; a display coupled to the image capture device to display the field of view; and a first component coupling the display with the kinematic component so as to display information on the tool represented in the field of view, the position of the information being based upon linkage structure data regarding the linkage; and the joint state information.

In still another embodiment, a method in a robotic system is provided. The method includes displaying a first image comprising a video feed of a tool supported by a robot within a field of view; and displaying a synthetic three-dimensional representation of the robot including the tool.

In another embodiment, a method in a robotic system is provided. The method includes displaying a first image comprising a video feed of a tool supported by a robot within a field of view, the first image consisting of a first portion of the robot; and displaying a synthetic three-dimensional representation of the robot including the tool, with the synthetic three-dimensional representation comprising a second portion of the robot that is greater than the first portion.

In yet another embodiment, a method is provided in a robotic system, the method including displaying a first image comprising a video feed of a tool supported by a robot within a field of view, the first image consisting of a first portion of the robot viewed from a first direction; and displaying a synthetic three-dimensional representation of the robot including the tool, with the synthetic three-dimensional representation viewed from a second direction.

DETAILED DESCRIPTION

In the following description, various aspects and embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted from this description or simplified in order not to obscure the embodiment being described.

Figure 1:
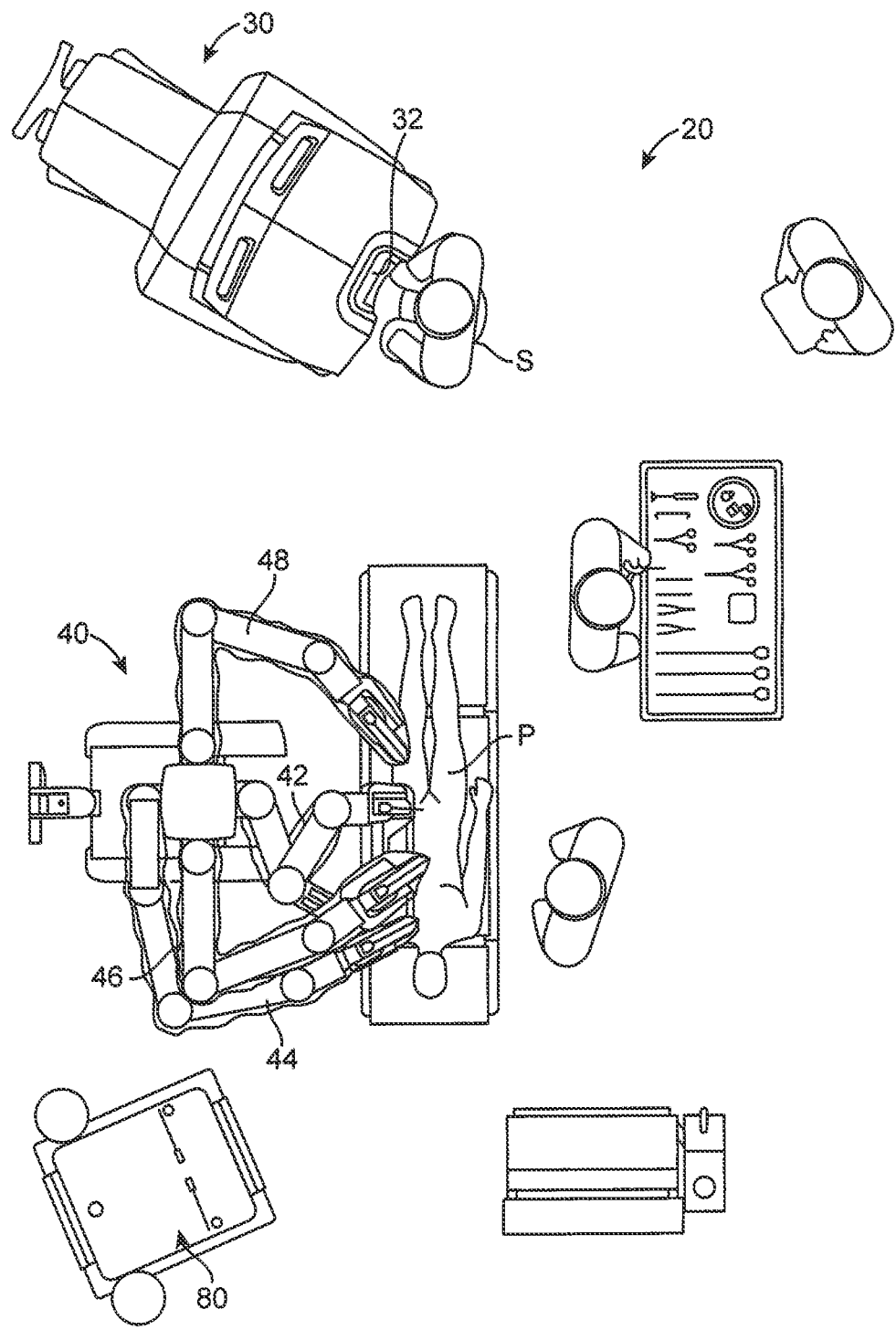
FIG. 1 shows a top view of an operating room which includes a minimally invasive telesurgical system.
Figure 5:
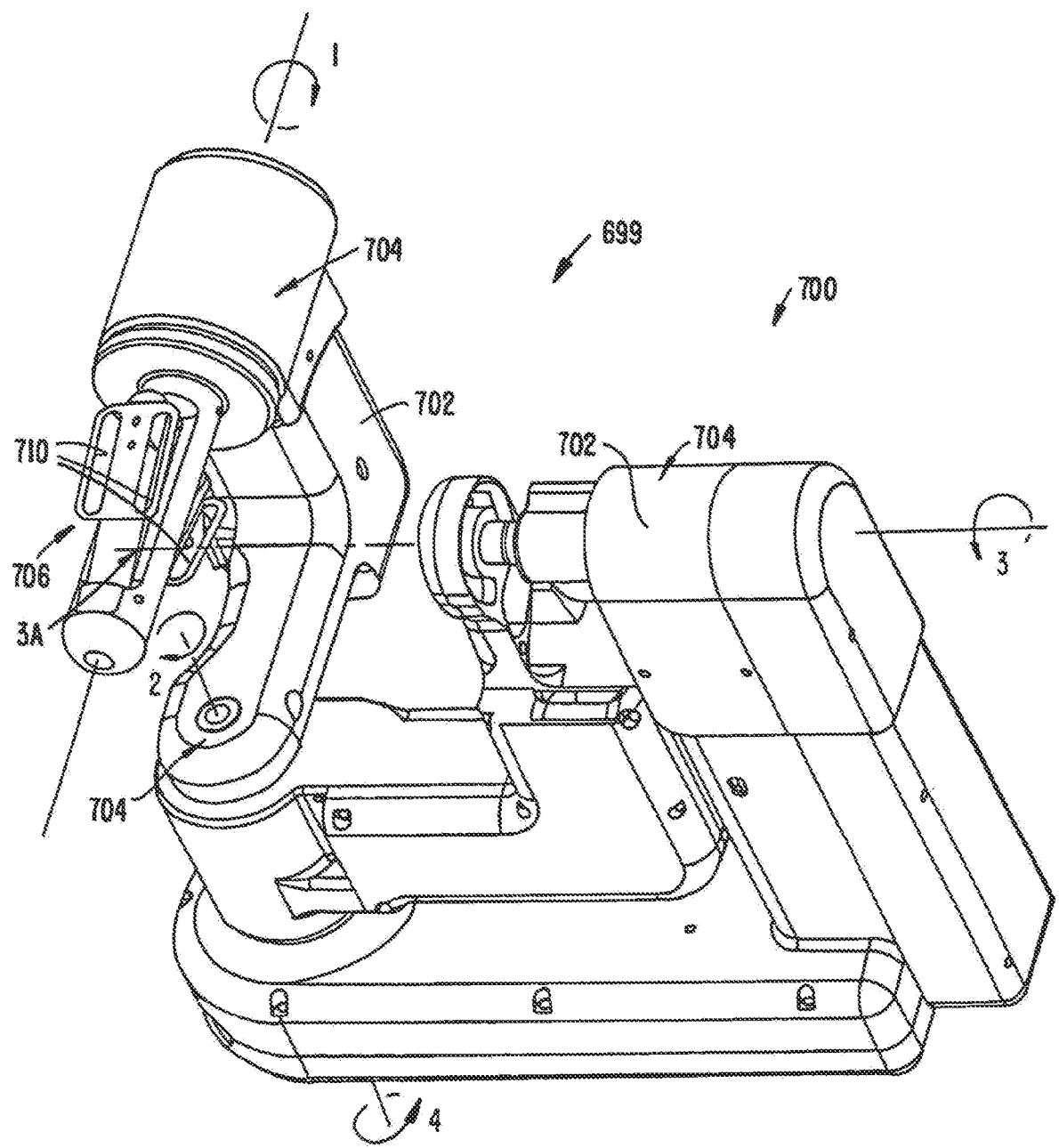
FIG. 5 is a side perspective view of a master controller.

Referring now to the drawings, in which like reference numerals represent like parts throughout several views, FIG. 1 shows a minimally invasive telesurgical system 20 having an operator station or surgeon console 30 in accordance with an embodiment. The surgeon console 30 includes a viewer 32 where an image of a surgical site is displayed to a surgeon S. As is known, a support (not shown) is provided on which the surgeon S can rest his or her forearms while gripping two master controls 700 (FIG. 5), one in each hand. More controls may be provided if more end effectors are available, but typically a surgeon manipulates only two controls at a time and, if multiple tools are used, the surgeon releases one tool with a master control 700 and grasps another with same master control. When using the surgeon console 30, the surgeon S typically sits in a chair in front of the surgeon console, positions his or her eyes in front of the viewer 32, and grips the master controls 700, one in each hand, while resting his or her forearms on the support.

A patient side cart 40 of the telesurgical system 20 is positioned adjacent to a patient P. In use, the patient side cart 40 is positioned close to the patient P requiring surgery. The patient side cart 40 typically is stationary during a surgical procedure, and includes wheels or castors to render it mobile. The surgeon console 30 is typically positioned remote from the patient side cart 40, and it may be separated from the patient side cart by a great distance—even miles away—but will typically be used within the same operating room as the patient side cart.

Figure 2:
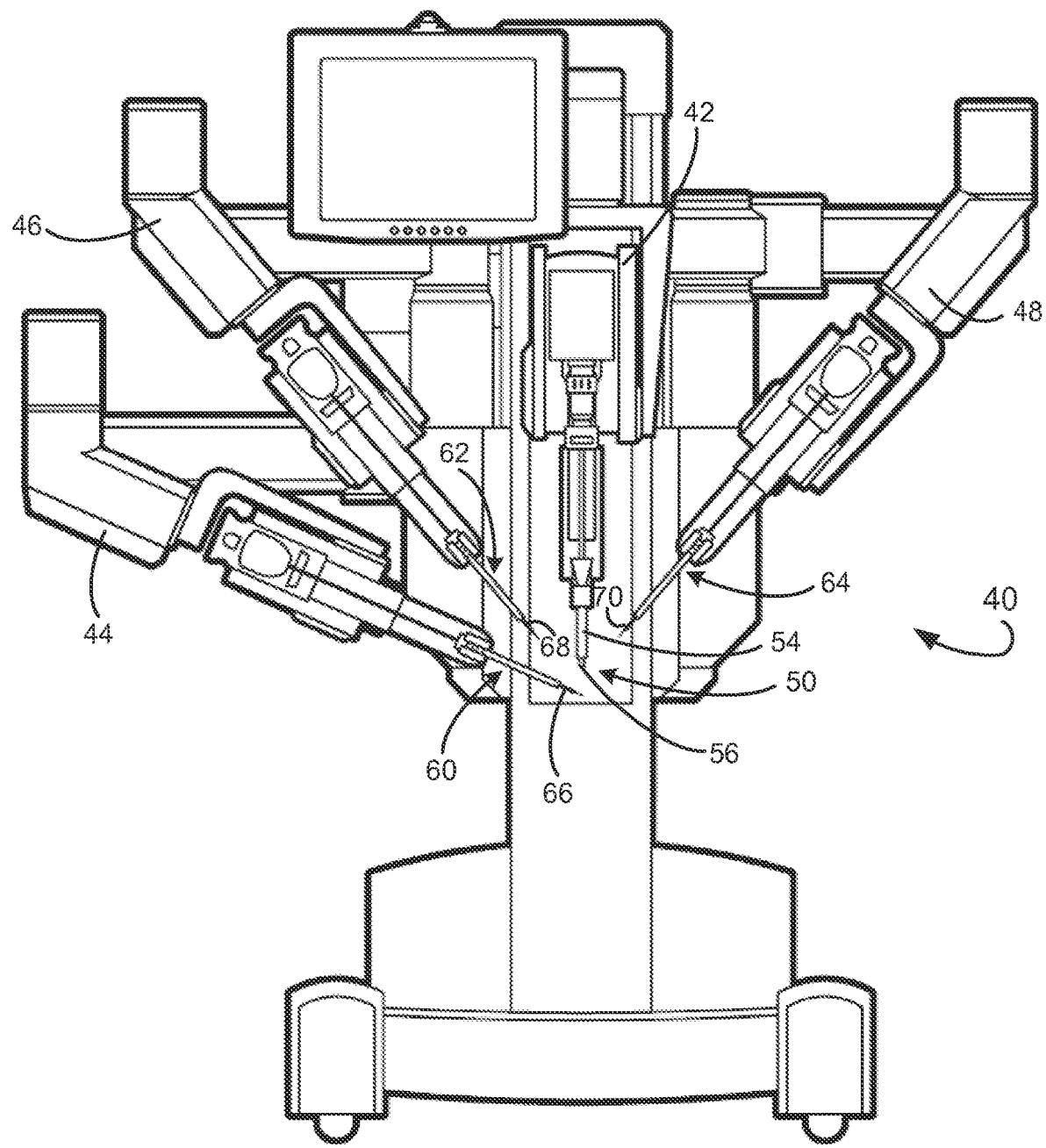
FIG. 2 is front view of a patient cart for the minimally invasive telesurgical system of FIG. 1.

The patient side cart 40, shown in more detail in FIG. 2, typically includes two or more robotic arm assemblies. In the embodiment shown in FIG. 2, the patient side cart 40 includes four robotic arm assemblies 42, 44, 46, 48, but more or less may be provided. Each robotic arm assembly 42, 44, 46, 48 is normally operatively connected to one of the master controls of the surgeon console 30. Thus, movement of the manipulator portion of the robotic arm assemblies 44, 46 48 is controlled by manipulation of the master controls.

One of the robotic arm assemblies, indicated by the reference numeral 42, is arranged to hold an image capture device 50, e.g., an endoscope, or the like. The endoscope or image capture device 50 includes a viewing end 56 at a remote end of an elongated shaft 54. The elongated shaft 54 permits the viewing end 56 to be inserted through a surgery entry port of the patient P. The image capture device 50 is operatively connected to the viewer 32 of the surgeon console 30 to display an image captured at its viewing end 56.

Each of the other robotic arm assemblies 44, 46, 48 is a linkage that supports and includes a removable surgical instrument or tool 60, 62, 64, respectively. The tools 60, 62, 64 of the robotic arm assemblies 44, 46, 48 include end effectors 66, 68, 70, respectively. The end effectors 66, 68, 70 are mounted on wrist members which are mounted on distal ends of elongated shafts of the tools, as is known in the art. The tools 60, 62, 64 have elongated shafts to permit the end effectors 66, 68, 70 to be inserted through surgical entry ports of the patient P. Movement of the end effectors 66, 68, 70 relative to the ends of the shafts of the tools 60, 62, 64 is controlled by the master controls of the surgeon console 30.

The depicted telesurgical system 20 includes a vision cart 80, which contains equipment associated with the image capture device. In another embodiment, the vision cart 80 can be combined with other equipment that includes most of the computer equipment or other controls (the "core" data processing equipment) for operating the telesurgical system 20. As an example, signals sent by the master controllers of the surgeon console 30 may be sent to the vision/core cart 80, which in turn may interpret the signals and generate commands for the end effectors 66, 68, 70 and/or robotic arm assemblies 44, 46, 48. In addition, video sent from the image capture device 50 to the viewer 34 may be processed by, or simply transferred by, the vision cart 80.

Figure 3:
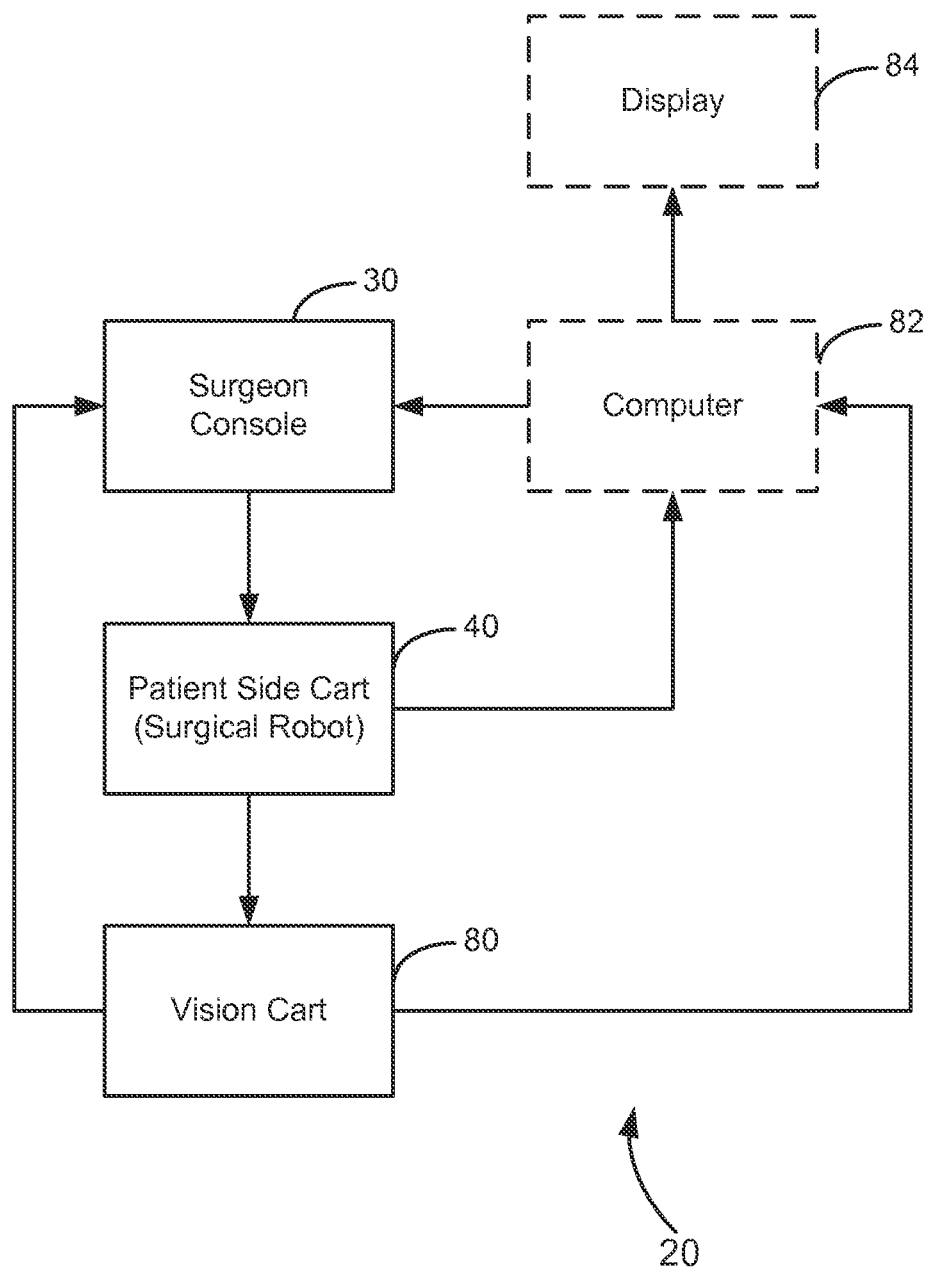
FIG. 3 is a block diagram representing components of the minimally invasive telesurgical system of FIG. 1.

FIG. 3 is a diagrammatic representation of the telesurgical system 20. As can be seen, the system includes the surgeon console 30, the patient side cart 40, and the vision cart 80. In addition, in accordance with an embodiment, an additional computer 82 and display 84 are provided. These components may be incorporated in one or more of the surgeon console 30, the patient side cart 40, and/or the vision cart 80. For example, the features of the computer 82 may be incorporated into the vision cart 80. In addition, the features of the display 84 may be incorporated into the surgeon console 30, for example, in the viewer 32, or maybe provided by a completely separate display at the surgeon console or on another location. In addition, in accordance with an embodiment, the computer 82 may generate information that may be utilized without a display, such as the display 84.

Although described as a "computer," the computer 82 may be a component of a computer system or any other software or hardware that is capable of performing the functions described herein. Moreover, as described above, functions and features of the computer 82 may be distributed over several devices or software components. Thus, the computer 82 shown in the drawings is for the convenience of discussion, and it may be replaced by a controller or its functions may be provided by one or more other components.

Figure 4:
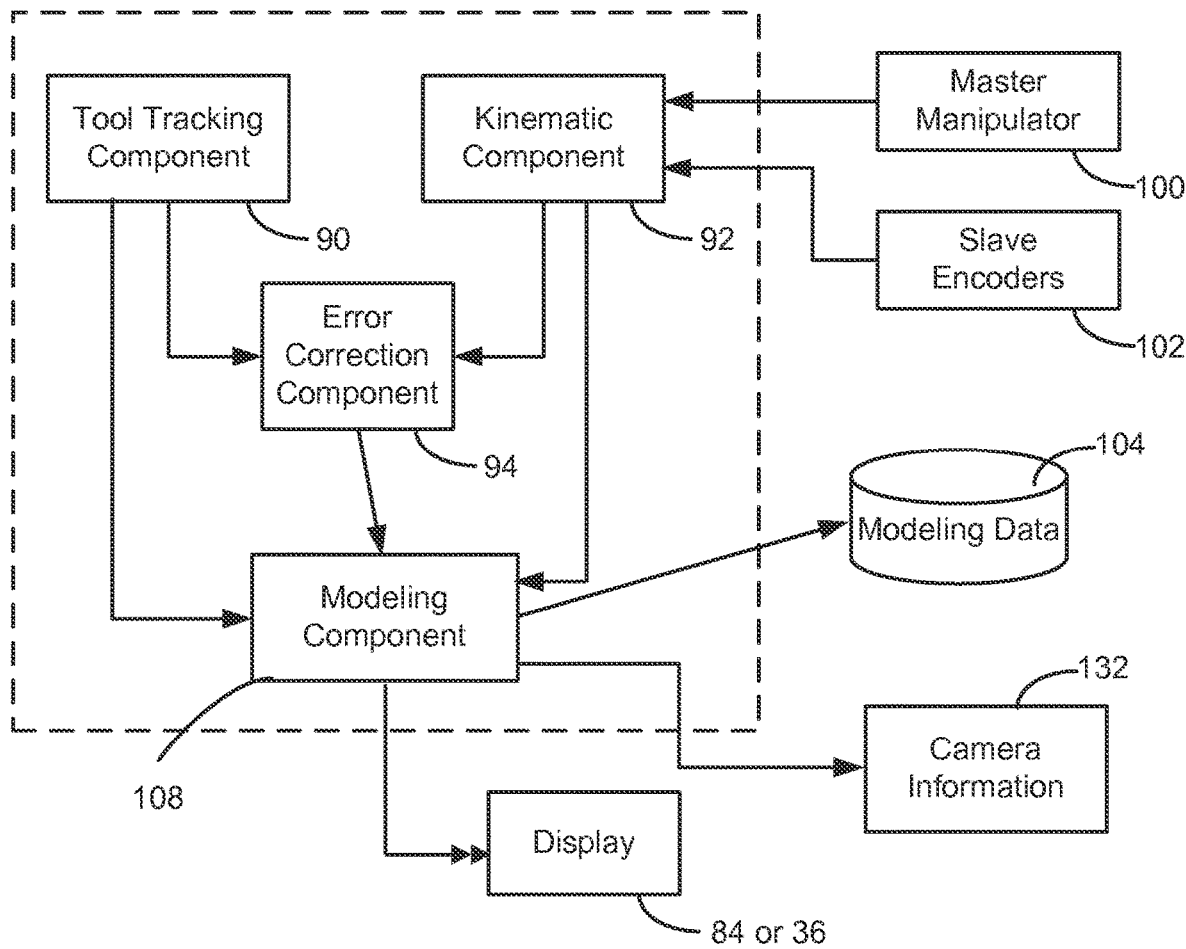
FIG. 4 is a block diagram representing components for a computer for use in the minimally invasive telesurgical system of FIG. 1.

FIG. 4 shows components of the computer 82 in accordance with an embodiment. A positional component is included in or is otherwise associated with the computer 82. The positional component provides information about a position of an end effector, such as one of the end effectors 66, 68, 70. In the embodiment shown in the drawings, a tool tracking component 90 is used for the positional component and provides information about a position of an end effector, such as the end effectors 66, 68, 70. As used herein, "position" means at least one of the location and/or the orientation of the end effector. A variety of different technologies may be used to provide information about a position of an end effector, and such technologies may or may not be considered tool tracking devices. In a simple embodiment, the positional component utilizes video feed from the image capture device 50 to provide information about the position of an end effector, but other information may be used instead of, or in addition to, this visual information, including sensor information, kinematic information, any combination of these, or additional information that may provide the position and/or orientation of the end effectors 66, 68, 70. Examples of systems that may be used for the tool tracking component 90 are disclosed in, U.S. Pat. No. 5,950,629 (filed Apr. 28, 1994), U.S. Pat. No. 6,468,265 (filed Nov. 9, 1999), U.S. Pat. App. Pub. No. US 2006/0258938 A1 (filed May 16, 2005), and U.S. Pat. App. Pub. No. US 2008/0004603 A1 (filed Jun. 29, 2006). In accordance with an embodiment, the tool tracking component 90 utilizes the systems and methods described in commonly owned U.S. Pat. App. No. 61/204,084 (filed Dec. 31, 2008). In general, the positional component maintains information about the actual position and orientation of end effectors. This information is updated depending upon when the information is available, and may be, for example, asynchronous information.

The kinematic component 92 is generally any device that estimates a position, herein a "kinematic position," of an end effector utilizing information available through the telesurgical system 20. In an embodiment, the kinematic component 92 utilizes kinematic position information from joint states of a linkage to the end effector. For example, the kinematic component 92 may utilize the master/slave architecture for the telesurgical system 20 to calculate intended Cartesian positions of the end effectors 66, 68, 70 based upon encoder signals for the joints in the linkage for each of the tools 60, 62, 64. As examples, the kinematic component may utilize slave encoders 102 and/or master manipulator encoders to estimate the position of tool. An example of system utilizing an embodiment of a kinematic component is described in U.S. Pat. No. 7,155,315, which is incorporated herein by reference, although others may be utilized. Kinematic position information for the end effector or any portion of the linkage and/or tool may also be provided in other ways, such as the use of optical fiber shape sensing, sensing the positions of components (e.g., electromagnetic components) embedded at various places along the linkage, tool, or end effector, various video tool tracking methods, etc.

In the embodiment shown in the drawings, an error correction component 94 is provided. In general, the error correction component calculates a difference between a location and/or orientation of a tool as provided by the tool tracking component 90 compared to the location and/or orientation of the tool as provided by the kinematic component 92. Because of the large number of joints and movable parts, current kinematics measurement typically does not provide exact information for the location of a surgical end effector in space. A system with sufficient rigidity and sensing could theoretically provide near-exact kinetic information. In current minimally invasive robotic surgery systems, however, often the kinematic information may be inaccurate by up to an inch in any direction when taken in space. Thus, in accordance with an embodiment, an offset may be generated by the error correction component 94. This offset provides information regarding the difference between the kinematic information provided by the kinematic component and the actual position information provided by the tool tracking component. Utilizing the offset, the kinematic information and the actual position information may be registered to the same location and/or orientation.

Figure 6:
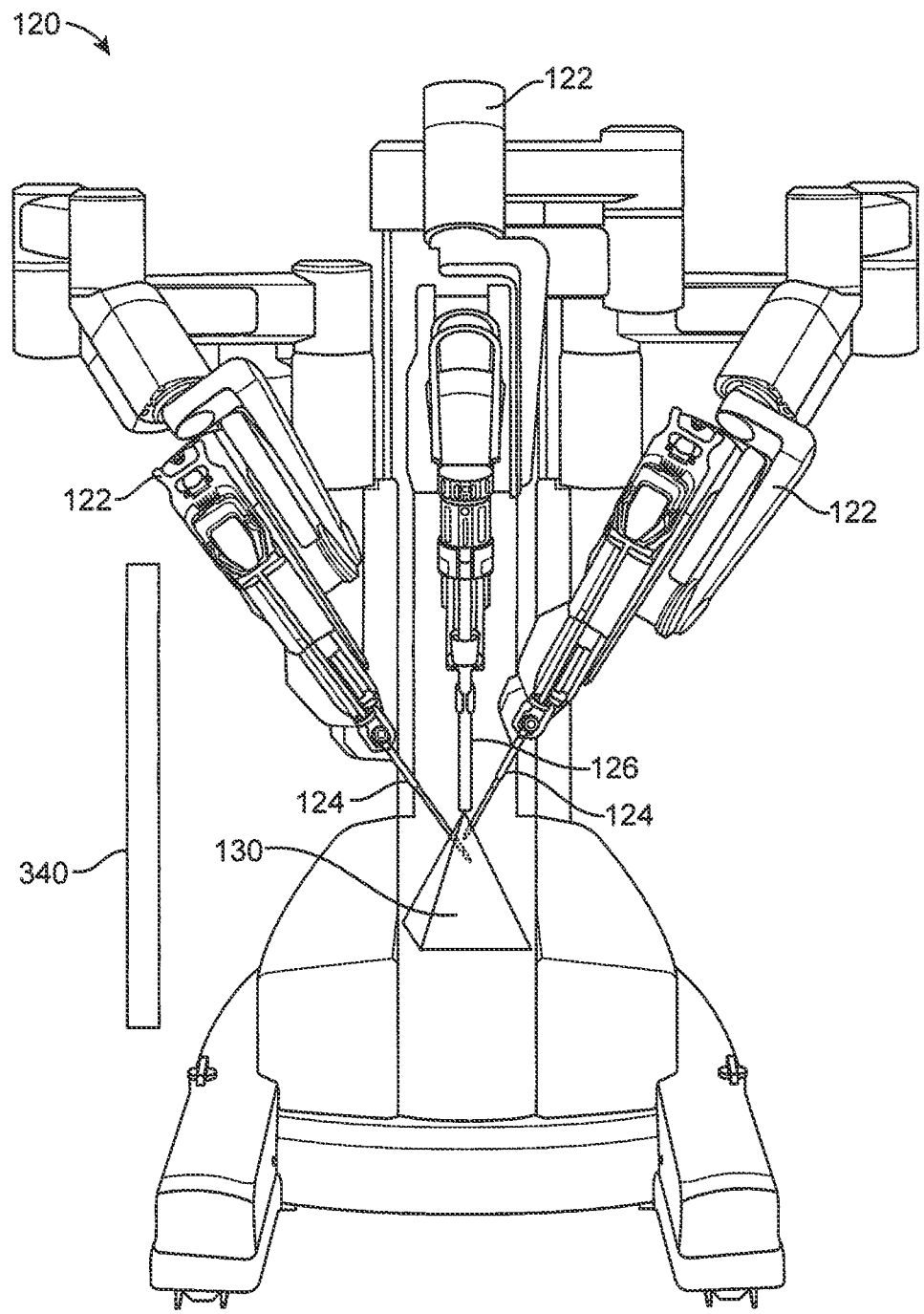
FIG. 6 is a view of a synthetic image of a robot.

In accordance with an embodiment, a modeling component 108 is provided for generating a synthetic image 120 (FIG. 6) of a patient side cart, such as the patient side cart 40, or any portion thereof. In the embodiment shown in the drawings, the synthetic image 120 is of a different patient side cart configuration than the patient side cart 40 (an illustrative model of a da Vinci® Surgical System Model IS2000 patient side cart with three arms is shown), but the basic components of the two patient side carts are the same, except that the patient side cart 40 includes an additional robotic arm assembly and tool. In accordance with an embodiment, the synthetic image 120 may be displayed on the display 84 or the viewer 32. To this end, modeling data 104 (FIG. 3) may be provided that is associated with the vision cart 80 and/or the computer 82. The modeling data 104 may be, for example, a two-dimensional (2-D) or three-dimensional (3-D) representation, such as an image, of the patient side cart 40, or any portion thereof. In an embodiment, such a representation is a 3-D model of the patient side cart 40, or any portion thereof, and thus may represent an actual solid model of the patient side cart 40, or any portion thereof. The modeling data 104 may be, for example, CAD data or other 3-D solid model data representing components of the patient side cart 40. In an embodiment, the 3-D model is manipulatable at each joint of the patient side cart 40, so that movements of the patient side cart may be mimicked by the synthetic image 120 of the patient side cart 40. The modeling data may represent the entire patient side cart or any portion thereof, such as only the tools for the patient side cart.

Joint locations and orientations are generally known from kinematic data provided, for example, by the kinematic component 92. Utilizing this information, each component of the patient side cart may be rendered in location so as to generate a image of the patient side cart that appears in 3-D to the surgeon. Thus, in an embodiment, the modeling data 104 includes individualized information for each component or link of the patient side cart robot.

In accordance with an embodiment, the modeling component 108 constantly updates the location and/or orientation of the components of the synthetic image 120 in accordance with information provided by the tool tracking component 90 and/or the kinematic component 92. For example, an initial state of the kinematic component 92 may be determined including a position of one or more end effectors for the patient side cart. These positions may be compared with position information provided by the tool tracking component 90. As described above, the difference between the actual position as determined by the tool tracking component 90 and the estimated position of the end effectors provided by the kinematic component 92 may result in an offset, which may be stored in or otherwise used by the error correction component 94. This offset may be used to register the position and orientation of an end effector as determined by the tool tracking component 90 to the position and orientation as estimated by the kinematic component 92.

As data is available from the tool tracking component 90, the actual position of the end effector may be tracked and registered with information provided by the kinematic component 92. When tool tracking information is not available from the tool tracking component 90, an assumption may be made that any change in kinematic information provided by the kinematic component 92 is an indication of actual movement by the end effector. That is, when tool tracking is not available, the position of an end effector may be accurately determined by the change in coordinate positions between the current position and the last known position, as calculated by the kinematic component 92. The assumption here is that the change in position may be accurately calculated using only kinematic data, without tool tracking information. This assumption is reasonable, because although kinematic information is often not accurate for calculating a position of an end effector in space, it is typically accurate for calculating a change of position once a position is known, especially over a short period of time or for a small amount of movement. Thus, asynchronous data may be provided by the tool tracking component 90, and synchronous data may be provided by the kinematic component 92. The combination of this information provides data regarding the positions and orientations of the components of the patient side cart 40.

The positions of the components of a robotic arm assembly may be determined by utilizing the joint states provided by the kinematic component. These joint states are calculated backwards from the end effector, the position of which is known, as described above. In addition, because the slave encoders 102 at the joints of robotic arm assemblies 122 for the patient side cart provide change in state information for each joint, the relative position of each section of the robotic arm assemblies may be accurately estimated and tracked. Thus, information can be provided to the modeling component 108 that is sufficient so that modeling component 108 may generate the synthetic image 120 by utilizing the modeling data 104, with the position of each of the segments of the robotic arm assemblies 122, including tools 124 at the end of the robotic arm assemblies, or an endoscope 126 at the end of one of the robotic arm assemblies.

Referring again to FIG. 6, in an embodiment, in addition to the synthetic image 120 for the patient side cart, a view volume 130 for the endoscope is provided. The view volume 130 represents a projection of the field of view of the endoscope 126. The field of view is the view visible by the endoscope, and the view volume is a projection of the boundaries of the field of view. That is, the view volume 130 represents a 3-D space that is visible by the endoscope 126. If desired, as shown in FIG. 4, camera information 132 may be provided to the modeling component 108. The camera information includes a calibrated set of intrinsic and extrinsic parameters about the camera. The intrinsic parameters include, e.g., focal length and principle point, which model the perspective mapping of the optics. Additionally, the intrinsic parameters may account for lens distortion. The extrinsic parameters may account for, e.g., relative position and orientation between the stereo endoscopic views. As can be understood, changing the parameters, such as zoom, of the endoscope will change the view volume for the endoscope, such as making the view volume narrower or wider. In addition, as the endoscope 126 is moved, the view volume 130 will move accordingly. The camera information permits the creation of a 3-D stereo rendering that may be superimposed on the stereo view of the end effector from the image capture device, as described below.

Figure 7:
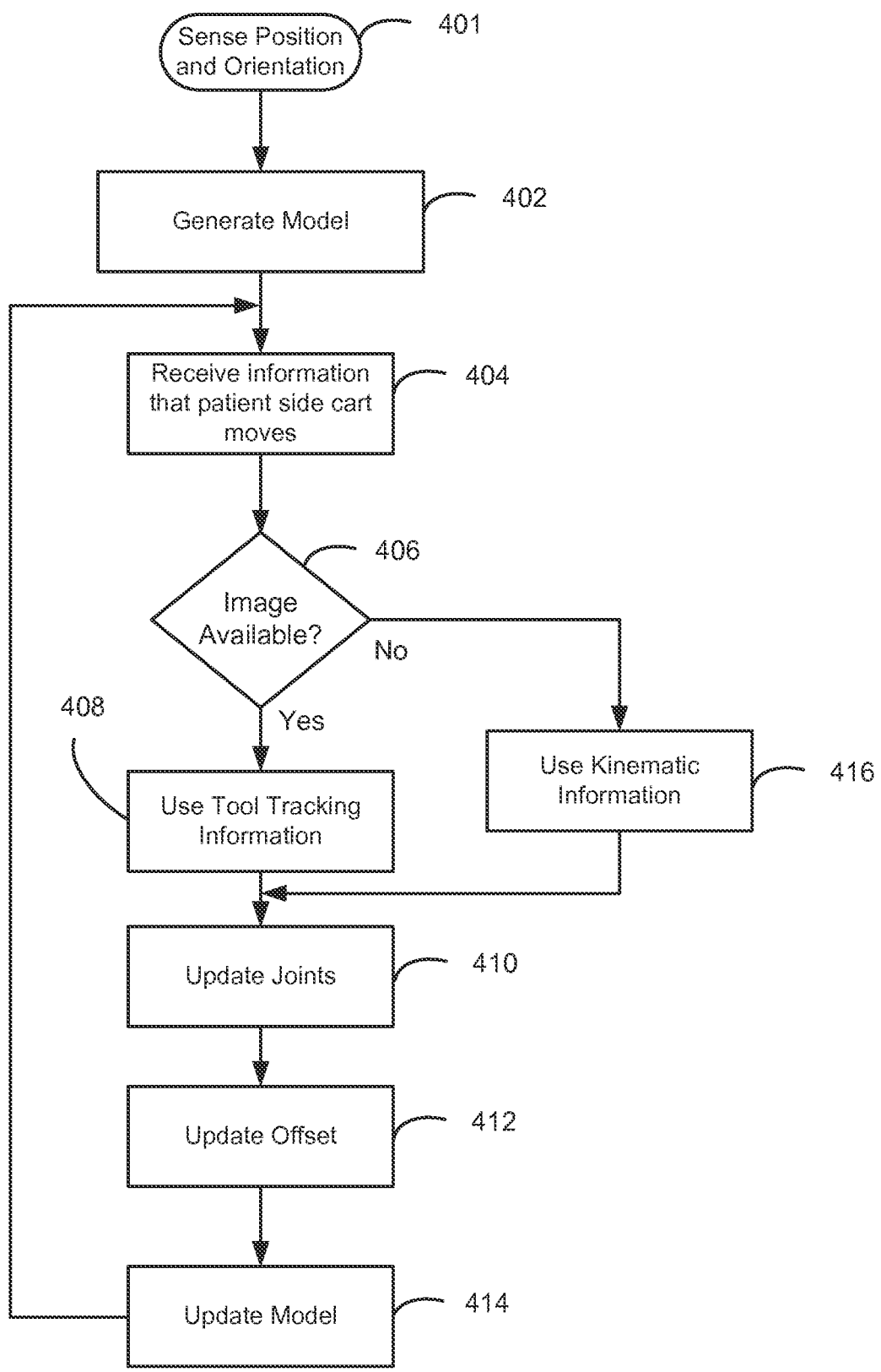
FIG. 7 is a flowchart representing a process for updating a rendering of a synthetic image.

FIG. 7 is a flowchart representing a process for updating a rendering of a synthetic image 120 in accordance with an embodiment. Beginning at 401, the position and orientation of the patient side cart, or any portion thereof, is sensed. This sensing may occur, for example, via the tool tracking component 90 and/or the kinematic component 92, as described above.

At 402, the position and orientation information from 401 is used to generate a model (e.g., the synthetic image 120). As described above, the modeling component 108 uses the modeling data 104 to generate the model. The position and orientation information provided from 401 is utilized to correctly arrange the position and orientation of the synthetic model to match that of the patient side cart.

At 404, as a result of the patient side cart moving, information is received. The movement may be, for example, movement of one of the robotic arm assemblies, movement of the endoscope, change in the focus of the endoscope, or movement by one of the end effectors. The movement of the end effector may be a change in location or orientation, including, for example, closing of pinchers or other operational movement of the end effectors.

At 406, a determination is made whether tool tracking information is available. In the embodiment show in FIG. 4, the determination is whether an image is available so that the actual position of the end effector or any portion of the tool that is in a field of view (e.g., the view volume 130) of the endoscope 126 may be found using the tool tracking component 90. In one aspect, if tool tracking is available, then 406 branches to 408 where the tool tracking information is utilized to update information about the position and orientation of the tool and/or end effector.

At 410, the kinematic information is used to update information about the location and orientation of the joints of each linkage of the robot for the patient side cart. At 412, the offset is updated, if desired. At 414, the display of the synthetic image 120 is updated, and the process branches back to 404.

At 406, if the tool tracking information is not available, then the process branches to 416, where the kinematic information provided by the kinematic component 92 is utilized to determine the position of the end effector. The process then proceeds to 410, and then on through the process, although since the tool tracking information was not available on this loop, the offset will likely not be updated, skipping 412.

Utilizing the method shown in FIG. 7, a 3-D rendering of the synthetic image 120 is generated, and the synthetic image accurately represents the physical configuration of the patient side cart at any point in time throughout a surgical procedure. This information can be utilized and viewed by the surgeon S, or by someone else, to evaluate the state of the patient side cart. As described below, the viewer 34 or the display 82 may show the synthetic image 120, either from a point of view that is the same as the point of view from the endoscope, or from another angle or distance. The synthetic image 120 enables observation of all parts of the patient view cart via the viewer 32, thus permitting the surgeon S to monitor movements of the robot and tools. In addition, in accordance with an embodiment, viewing of these components is available in connection with the view volume 130, permitting a surgeon to have a good perspective of where the endoscope's field of view is with respect to space. The view volume 130 provides a three dimensional representation of what is being seen by the surgeon S when looking in the viewer 32.

Figure 8:
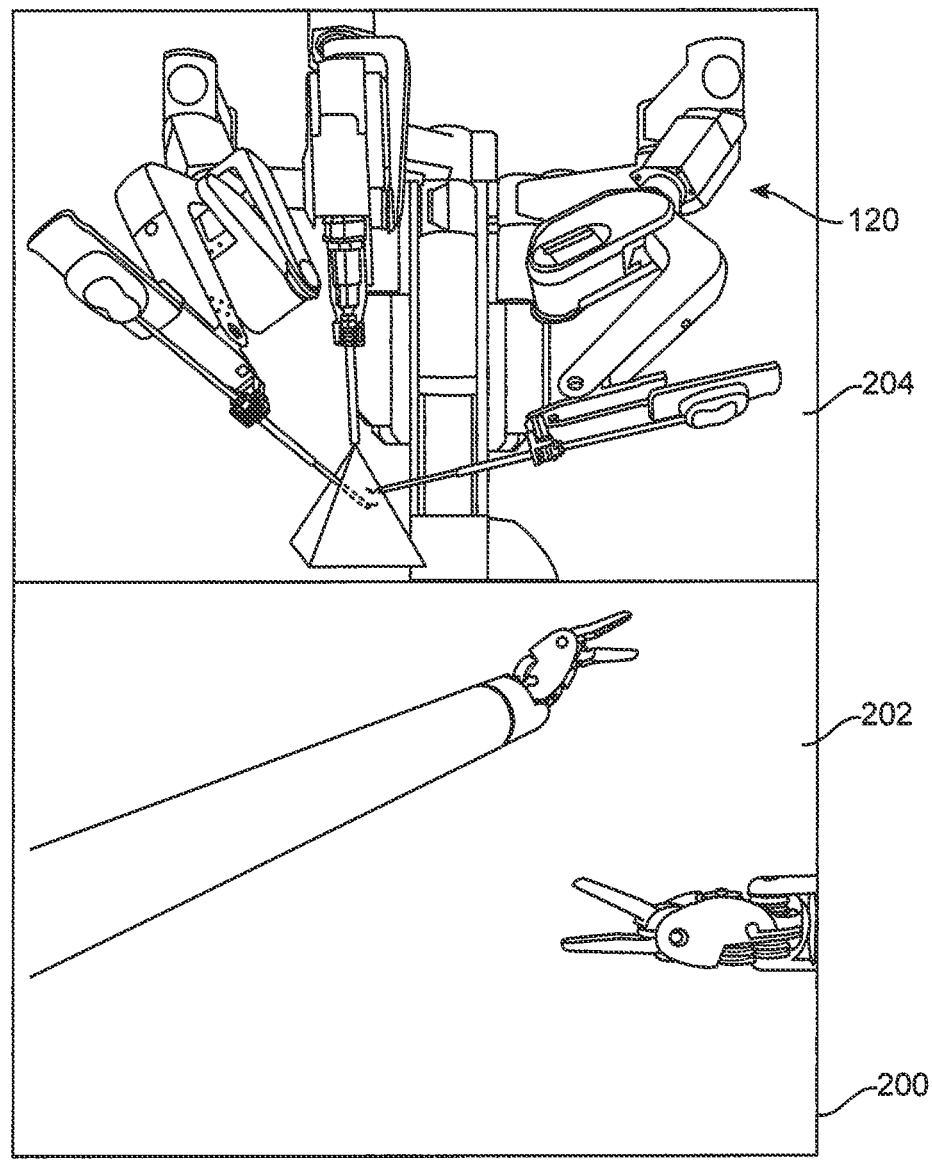
FIG. 8 is a view provided by a display that provides both a field of view for an endoscope and a synthetic image of a robot supporting the endoscope.

If desired, a single display may be provided for showing both the field of view of the endoscope and the synthetic image 120. For example, as shown in FIG. 8, a view 200 provided by the viewer 32 or the display 84 provides both an actual field of view image 202 for the endoscope 126 and the synthetic image 120. The synthetic image 120 is shown in a separate tile window 204. In the embodiment shown in FIG. 8, the tile 204 is approximately the same size as the field of view 202, but if desired, the tile window may be smaller or larger than the field of view 202. Also, if desired, a toggle or other feature may be provided so that the surgeon may switch back and forth between a larger presentation of the synthetic image 120 or the field of view 202. In addition, the synthetic image 120 and/or the tile window 204 may be partially superimposed over a portion of the field of view, either on a continuous basis or upon request.

As an example of toggling back and forth between a larger presentation of the synthetic image 120 or the field of view 202, a camera control may be provided that is connected to the master manipulators. For example, a user may start looking at the endoscopic view and may pull the endoscope back by pulling the his hands towards himself while in a camera control mode. At some point, the endoscope cannot be pulled back any farther, and the field of view encompasses a maximum area. Continuing to pull back on the master controls (with or without a haptic detent or other indication) can expose a view showing sections of a synthetic image 120 along the borders of the real image (e.g., the image captured in field of view 202). Pulling back even farther on the master controls (with or without haptic detent or other indication) may provide a view where the image captured in field of view 202 is only the middle section of the screen. Pulling back still farther on the controls (with or without haptic detent or other indication) may provide the entire synthetic image 120. Reversing the master control direction can be used to reverse such a real-to-synthetic zoom out function and control a synthetic-to-real zoom in function. As an alternative to camera control using master manipulator movement, the system may be configured to use another control input (e.g., a foot pedal, a finger button on a manipulator, the roll of the master manipulator grip, and the like) to control the zoom functions.

Figure 9:
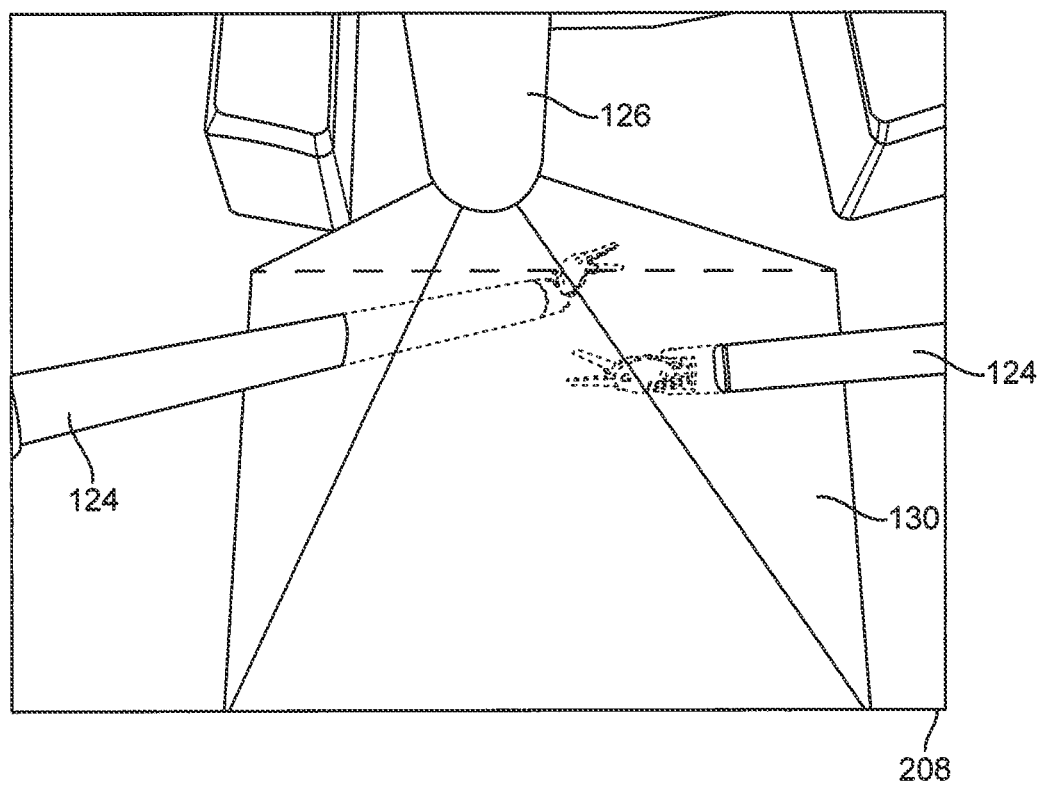
FIG. 9 shows a tile window displaying an alternate angle for viewing a portion of the synthetic image of a robot.

FIG. 9 shows a tile window 208 displaying an alternate angle for viewing a portion of the synthetic image 120. In the embodiment shown, the view volume 130 is slightly tilted from the actual field of view of the endoscope, but the particular angle of view of the view volume 130 shows relevant information regarding the configuration of the tools 124 with respect to the view volume.

The features of the synthetic image 120 provide another number of benefits to a user of the minimally invasive telesurgical system 20. Some of these advantages are set forth below.

Collision Detection

Typically, in a minimally invasive telesurgical system, only the most distal portions of the surgical tools, such as the tools 124, may be visible to the surgeon in the field of view of the endoscope 126 at any time. Depending upon the configuration of the patient side cart, it is possible that collisions between moving parts of the robot assembly may occur which are not visible to the surgeon in the field of view. Some of these collisions ("outer collisions" because they are outside of the field of view for the endoscope 126) may occur between the linkages of robotic arm assemblies leading to the tools, the collisions may occur between two tools, or may occur between a tool and a linkage. Such outer collisions may occur outside the body or inside the body but not within the field of view. In addition, an outer collision may occur between one tool that is in the field of view and another tool that is slightly outside the field of view. Collisions occurring inside the body and in the field of view of the endoscope are "inner collisions".

In accordance with an embodiment, the synthetic image 120 and/or the information generated by the modeling component 128 may be utilized for collision detection. As an example, a surgeon viewing the viewer 32, or another individual viewing the display 84, may view the synthetic image 120 to see an indication of an imminent or actual collision.

Collision detection may involve more than just a visual image of a collision. Information about relative locations of robot linkages and tools is maintained by the modeling component 128, and this information may be used to generate a signal if two components are sensed to be too close to one another. For example, each tool may be treated like a capsule or cylinder, having a particular radius or buffer zone outside the tool's surface. Using the actual position information from the tool tracking component and/or the kinematic information from the kinematic component 92, the modeling component 108 may predict or warn of a collision. For example, if two tools 124 are presumed to have a radius of one half inch each, then if the center line for one of the tools comes within an inch of the center line for a second tool, then the modeling component 108 may assume that a collision has occurred. A separate signal may be generated if the two tools are calculated to be close, but not in contact, with each other. For the above example, this distance may be, e.g., a center line distance between the tools of 1.20 inches.

Figure 10:
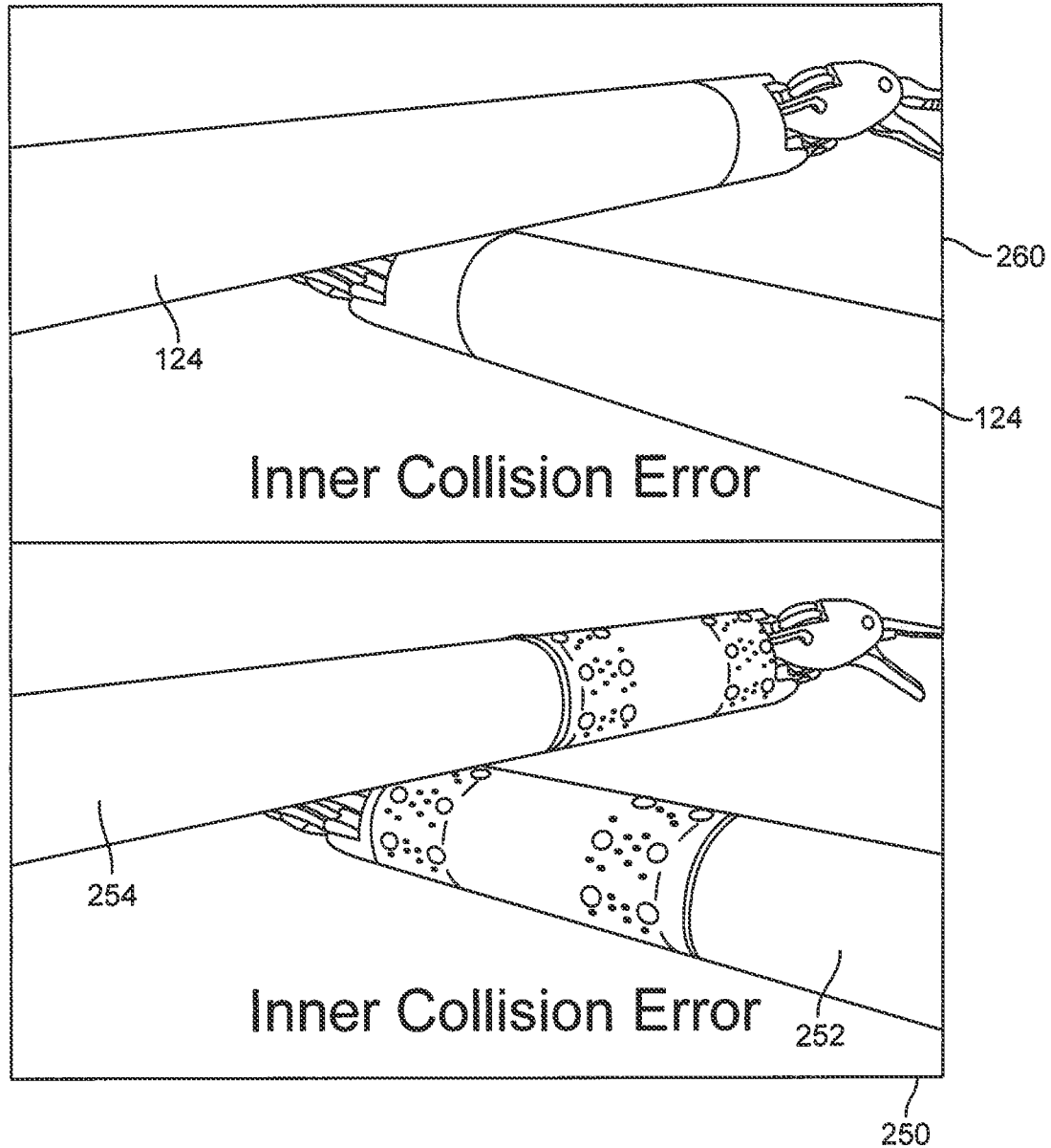
FIG. 10 shows a field of view in which two tools are colliding.

FIG. 10 shows at the bottom a display tile window in which a real field of view image 250 shows two tools 252, 254 colliding. Although the collision in FIG. 10 is within the field of view 250, as described above, the collision may take place outside the field of view or even outside the body of the patient. Even if inside the field of view, the tools 252, 254 are not necessarily visible, because they may be blocked by cauterization smoke, blood, or an organ, as examples. In FIG. 10, the inner collision is seen in the field of view 250, but it is also detected by the modeling component 108.

At the top of FIG. 10 is a display tile window 260 representing the synthetic image 120. In the embodiment shown in FIG. 10, the tile window 260 is taken from the same point of view as the field of view 250, but a different point of view may be provided as described above. In addition, as described above, outer collisions, as well as inner collisions, may be detected.

Figure 11:
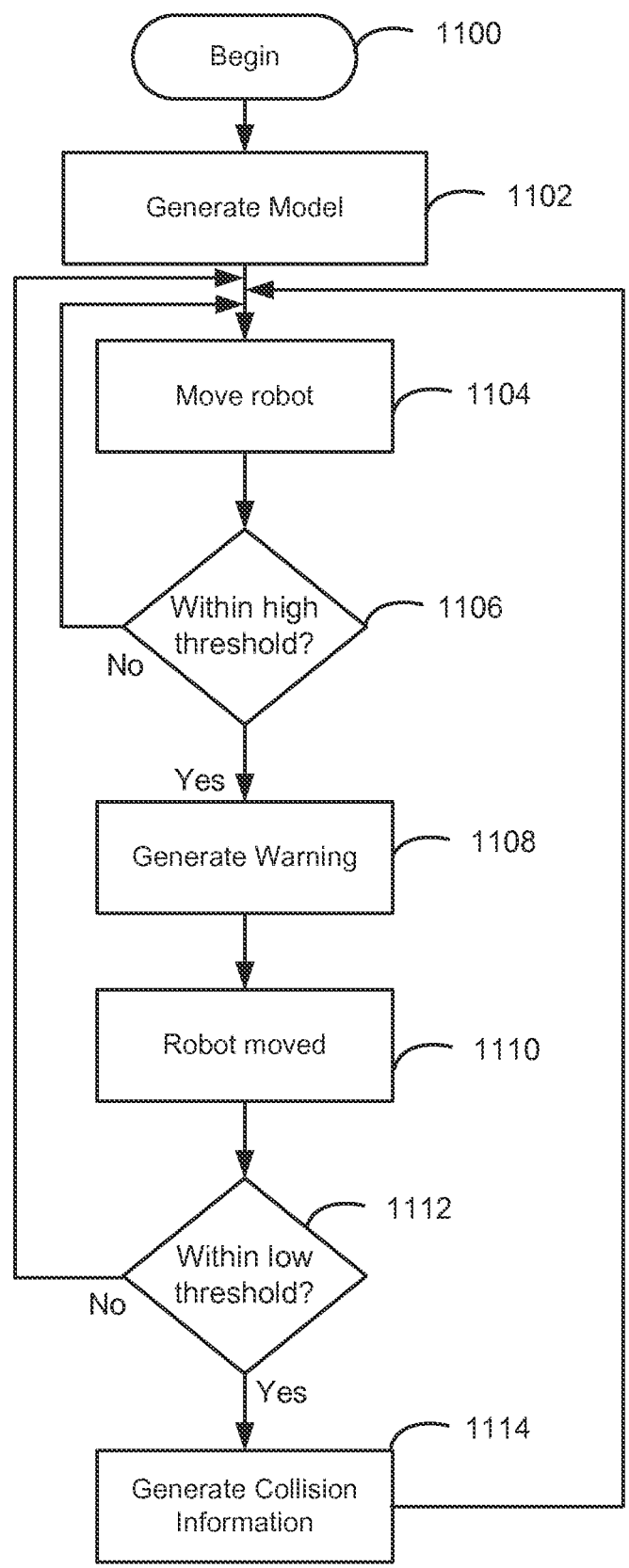
FIG. 11 is a flowchart showing a process for providing collision information.

FIG. 11 is a flowchart showing an illustrative process for providing collision information in accordance with an embodiment. The process begins at 1100. At 1102, a model, such as the synthetic image 120, is generated. This generation process is described with reference to FIG. 7. At 1104, the robot for the patient side cart is moved. At 1105, the proximity of linkages and/or tools of the robotic arm assemblies 122 are computed. At 1106, a determination is made whether the proximities are within a high threshold. The high threshold represents spacing between tools or linkages at which a warning of a collision is given. For example, as described above, if two tools are assumed to have a radius of a half an inch, the high threshold may be a centerline separation of 1.2 inches. If the components of the patient side cart are not within the high threshold, 1106 branches back to 1104, and the robot continues to move.

If two components of the patient side cart are within the high threshold, then 1106 branches to 1108, where a warning is generated. This warning may be an audible warning, a visual warning (e.g., provided within the viewer 32 or on the display 84), or another suitable indication of collision proximity. If visual, the warning may be presented, for example, in the field of view 250 (FIG. 10). In the embodiment shown in FIG. 10, the words "inner collision error" are shown, indicating an actual collision. Alternatively, for a warning message, a message stating that tools are too close or similar may be provided. In addition, for the view of the synthetic image 120, the color of the tools 124 may change to provide the warning, such as changing from a metal color to yellow for a warning.

A surgeon may or may not elect to rearrange the robot after the warning is generated at 1108. In either event, the process proceeds to 1110, where the robot has moved again. At 1112, a determination is made whether the robot is within a low threshold. In an embodiment, the low threshold represents a distance, such as a center line distance, at which a collision is assumed. If the low threshold is not met, the process branches back to 1104 and continues to loop, likely continuing to generate the warning message unless the components of the patient side cart are moved to outside the high threshold in 1106.

If the components are within the low threshold, then 1112 branches to 1114, where collision information is generated, such as a collision warning or message. As an example, in FIG. 10, the collision error warning is provided in the field of view 250. (Both near and actual collision warnings may use the same or different indications.) A similar collision error warning may be provided in the tile window 260, and the tools 124 may change colors, such as to red, to show a collision error. The process then loops back to 1104.

As stated above, for collision detection, the components need not be in the field of view of the viewer 32. Thus, when components of the patient side cart are improperly aligned and are approaching a collision or actually have a collision, information may be provided, either in visual form or in the form of a warning or error message. The warning may be particularly helpful where a user is not familiar with operation of the robot and may put the tools or robotic arm assemblies in an awkward position. The person viewing the viewer 32 may select a different synthetic view angle and distance of the robot so as to determine the near collision or actual collision point between two robotic manipulators. Once the operator views the collision point, he or she may adjust one or more of the robot's kinematic arms (either the passive, "set up" portions or the actively controlled, manipulator portions) to cure the actual or near collision condition and avoid further collisions. In one aspect, if the operator is viewing a synthetic view that corresponds to the endoscope's field of view, the synthetic view may be automatically changed to show a collision point if a collision warning or actual collision is occurring.

In an embodiment, the location of a patient and/or portions of the patient's tissue structures (e.g., from preoperative imaging or by other suitable method of registering tissue structure locations) may be provided to the system, and registered patient location data may be to detect, warn, and display actual or potential collisions between the robot and the patient or designated tissue structures in the patient. Collisions may be detected as described above.

Also, in an embodiment, a visual, audio, or other indicator may be provided to assist in reducing or correcting a collision state. For example, for the warning situation described above, information may be provided to a surgeon to aid the surgeon in avoiding a collision. For example, a visual indicator may provide information about a movement direction in which a collision might occur, or may indicate a movement direction for the surgeon to make in order to avoid or cure a collision.

Lost Tool Recovery

In minimally invasive surgery, it is possible for instruments to be positioned outside the endoscopic camera's view volume. This possibility can result in situations where the tool is effectively lost, since the surgeon does not necessarily know how to move the endoscope to bring the instrument back into view, or how to move the instrument into the endoscope's field of view. Moreover, the situation may compromise patient safety, since the surgeon is able to move an instrument which cannot be observed.

[The synthetic image 120 provides a solution to this problem by presenting the surgeon with a broader view of the endoscope's view volume 130, along with an accurate depiction of the position of each tool 124. Such a broader view and tool depiction may be provided from various points of view. In an embodiment, the broad view and tool depictions are provided from the same point of view or direction as the endoscope field of view. By providing a broad view in this direction, the surgeon will be able to retain the intuitive tool control movement he or she normally experiences when viewing the real endoscopic image while moving tools into the proper position so that the tool is back in the view volume 130. Alternatively, the view volume 130 may be viewed from other angles, allowing a surgeon to have a different perspective of what the endoscope 126 is viewing. As examples, FIGS. 8 and 9 show three different views, taken at different angles and pans, of views that may be shown for the synthetic image 120. Although the lower part of FIG. 8 shows an actual image, a synthetic image 120 may be provided from the same direction, and would look similar except that synthetic tools would be shown instead of video feed of the actual tools. The view established by the field of view is shown in the lower part of FIG. 8, and a view taken from a front side of the synthetic image—zoomed outward to show much of the patient side cart—is shown in the top of FIG. 8. A view taken slightly rearward and upward of the direction of the field of view of the endoscope, and zoomed outward to show the view volume 130, is shown in FIG. 9. This slight variation in view provides a good perspective of where the tools 124 are with respect to the view volume 130. A surgeon may toggle between a view consistent with the field of view and one just off from the field of view, such as shown in FIG. 9. To this end, a controller or other device may be provided for allowing a surgeon to toggle between different views of the synthetic image 120. Alternatively, a separate controller or the master controller may be utilized to allow infinite positioning (e.g., various pan, tilt, roll, dolly, truck, crane, and zoom image movements) of the synthetic image 120.

Figure 12:
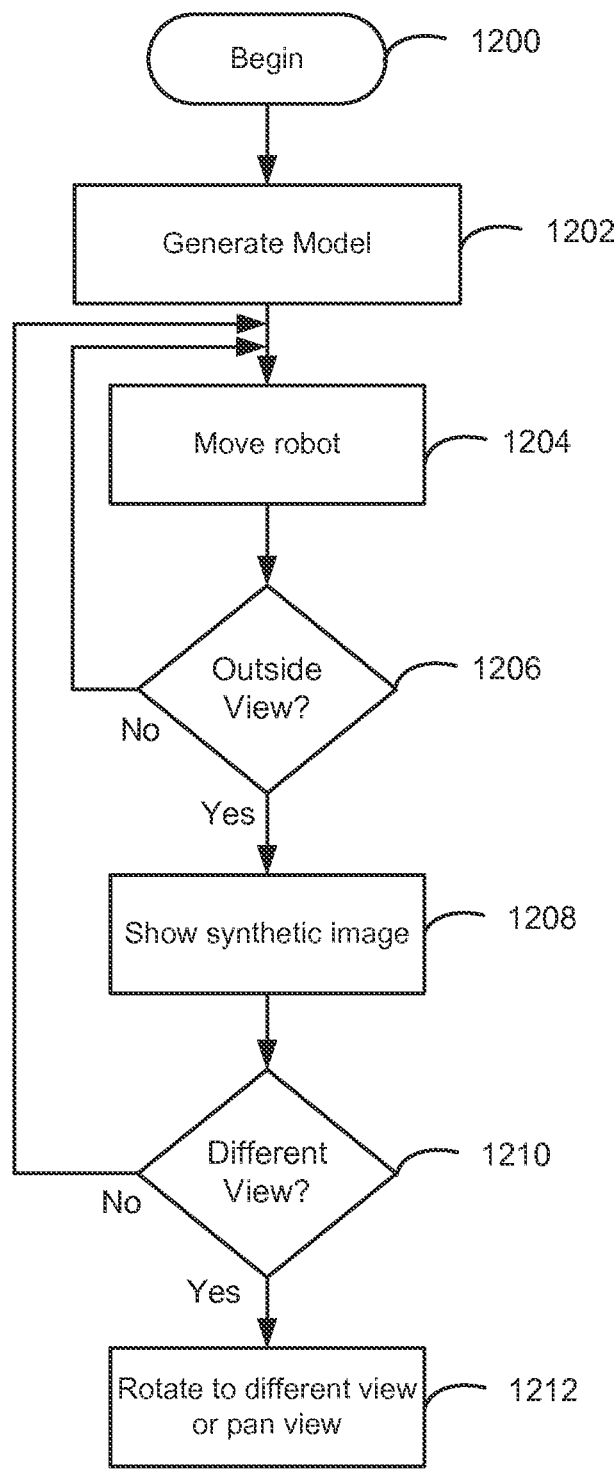
FIG. 12 is a flow chart representing a process for lost tool recovery.

FIG. 12 is a flow chart representing a process for lost tool recovery in accordance with an embodiment. The process begins at 1200. At 1202, the synthetic image 120 is generated as described above. At 1204, the patient side cart, or the robot, is moved.

At 1206, a determination is made whether one or more of the tools is outside of the field of view. If not, the process loops back to 1204. If one or more of the tools is outside of the field of view, then the process may move to 1208, where a synthetic image is shown. The synthetic image may or may not be automatically shown; the synthetic image display may be selected by a surgeon. To this end, 1208 may be done as a result of a request by the surgeon or another operator, and may or may not be triggered by a tool being out of the field of view. If desired, however, a synthetic image may be automatically shown as a result of a loss of an image of the tool. In such an embodiment, however, it may be desirable to show the synthetic image in a tile window in addition to the field of view, instead of taking the field of view away from the surgeon.

If the missing tool display option is available, the synthetic view 120 may be requested or otherwise provided in 1208. The synthetic image provided in 1208 may be, as described above, substantially the same as the field of view of the endoscope 126 or any number of perspectives of the modeled system. If a desired angle is not shown, then a surgeon may elect at 1210 to show a different view. If the surgeon elects to show a different view, then 1210 branches to 1212, where the synthetic image 120 is, e.g., rotated to show a different view. If desired, as part of this movement, the synthetic image may rotate in space so that the surgeon may get an idea of the position from which the view started relative to the position where the view is going. In addition, in accordance with an embodiment, when a view of the synthetic image 120 is inconsistent with the same point of view as the field of view, a warning message or other indicator may be provided to the surgeon so that the surgeon may understand that he or she is looking at the view volume 130 from a direction that is different than the direction of the field of view.

If the surgeon did not request a different view in 1210, then the process loops back to 1204.

As described above, the synthetic image 120 provides an image of the patient side cart that is larger than and outside of the view volume 130. Thus, even if taken along the same point of view as the field of the view of the endoscope 126, the surgeon may zoom outward so that tools that are just outside the view volume 130 may be seen. The surgeon may then move these tools or the endoscope to the desired position so that they are within the field of view.

Mixed Video and Rendered View

As described above, there are a number of ways in which the system may present the synthetic image 120 of the robot to the surgeon. A first option, described with respect to FIG. 8, includes a tile window 204 showing a synthetic view above the field of view image 202, with both shown at the same time. Another option, shown in FIG. 9, shows only the synthetic image 120.

In accordance with an embodiment, a third option is provided in which a video display from an endoscope is superimposed over the synthetic image 120, with the positions matched, so that the video image is rendered in the context of the synthetic image 120 of the entire patient side cart. This view provides relative positions of the components of the patient cart for the surgeon, and allows the surgeon to understand where the surgeon is with respect to space. The view is also well suited when transitioning between a pure video display and a pure synthetic image 120. During the transition, the surgeon can relate respective positions of the robot and the video image from the endoscope.

Figure 13:
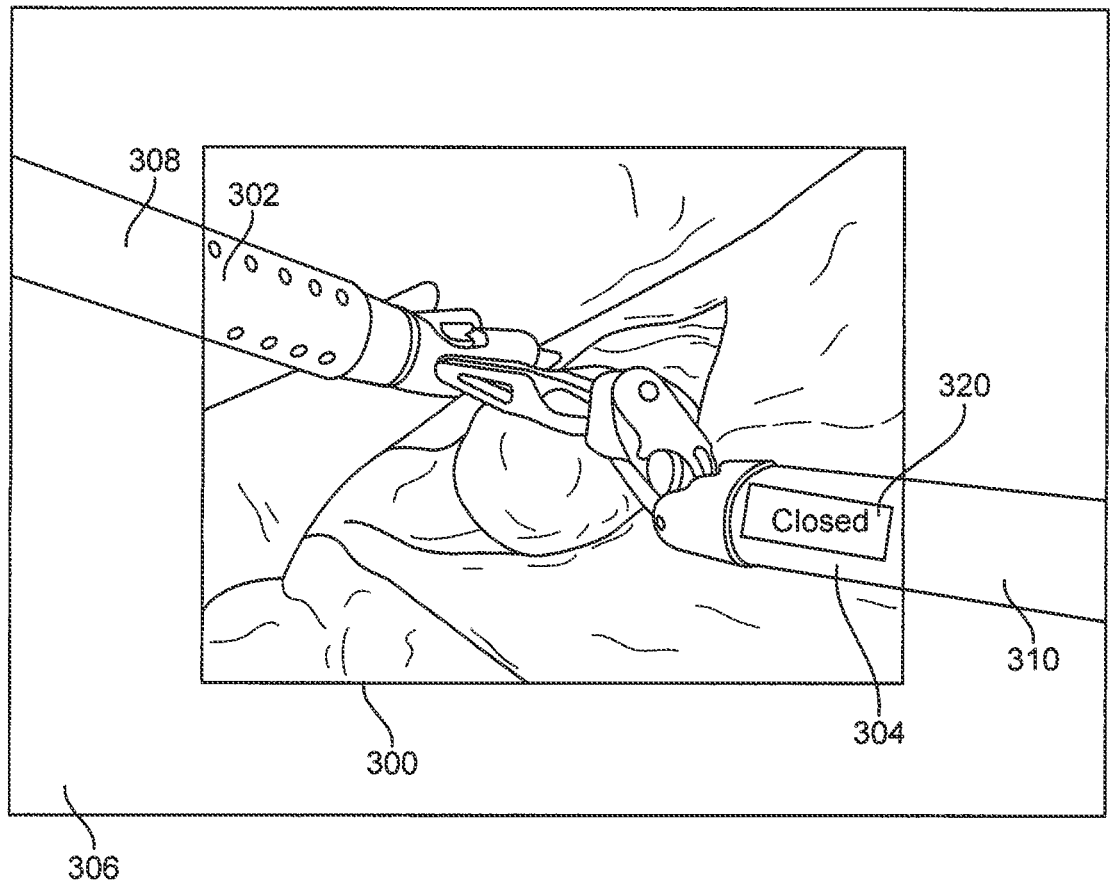
FIG. 13 shows a field of view projected over a window tile that includes a synthetic image of a robot.

A simplified version of this feature is shown in FIG. 13, where an image within the field of view 300 is projected over a window tile 306 that includes the synthetic image 120. The field of view image 300 includes two tools 302, 304 performing an operation. The window tile 306 extends the view provided by the field of view 300, and additional sections of the tools 302,304—indicated by the reference numerals 308,310, respectively—are provided. The surgeon may zoom in and out to provide additional information about the location of the tools with respect to other parts of the patient side cart. In addition, the features described with respect to the embodiment shown in FIG. 13 may be utilized to find the lost tool that is just outside the field of view, for example, in the window tile 306, but not in the field of view 300.

Visual Troubleshooting Indicator

In accordance with an embodiment, instead of or in addition to the synthetic image 120, the modeling data 104 may be utilized to project a image other than a visual representation of portions of the patient side cart. For example, using the position information provided by the tool tracking component 90 and/or the kinematic component 92, the modeling component 108 may display a portion of the synthetic image 120 in a different color, or it may display text on a portion of the synthetic image or instead of the synthetic image. In such an embodiment, the text may be superimposed over the actual tools in a field of view so as to focus attention on that tool or to provide other information. As an example, for the tool 304 in FIG. 13, the modeling component 108 may be utilized to display a text message "closed" 320 collocated over the video image of the tool 304 to indicate that the clamp for the tool is closed. The camera information, described above, permits the creation of a 3-D stereo rendering that may be superimposed on the stereo view of the tool 304 from the image capture device. Error messages may also be provided.

Figure 14:
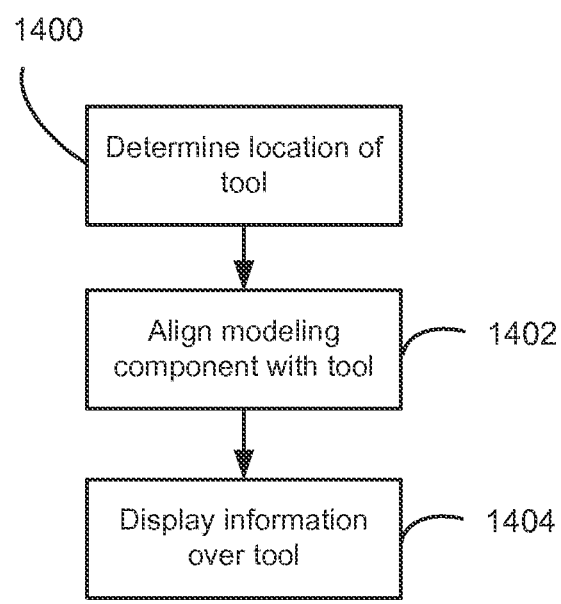
FIG. 14 is a flow chart representing a process for displaying information utilizing a modeling component.

FIG. 14 is a flow chart representing a process for displaying information utilizing the modeling component 108 in accordance with an embodiment. Beginning at 1400, the location of the components of the patient side cart is determined, for example, the location of the tools 124. At 1402, the modeling component 108 is aligned with the tool as described above. At 1404, the desired information is displayed over the tool. For example, as described above, words may be displayed over the tool. In addition, if desired, information may be displayed around or adjacent to a tool or other feature.

As can be understood, to superimpose a message over actual tools in the field of view, the modeling data 104 need only include information about the outer perimeter of the tools. The other components of the patient side cart are not needed for this embodiment.

Communication Aid

The synthetic image 120 may be useful in providing a remote image of the operation of the patient side cart. For example, in some situations, an individual remote from the patient side cart may desire to view operation of the patient side cart. In such a situation, the synthetic image 120 may be rendered at both the viewer 32 and a remote display (e.g., the display 84). In such a situation, in accordance with one embodiment, the modeling data may be maintained all at one location, with the synthetic image 120 sent to a remote location for display at the remote location.

In an alternate embodiment, position and orientation information provided by the tool tracking component 90 and/or the kinematic component 92 may be sent to a remote computer. The remote computer, in turn, includes a modeling component 108 and the modeling data 104. In this embodiment, the synthetic image 120 is generated at the remote location in a separate operation from producing the synthetic image 120 for the viewer 32.

Being able to provide a synthetic image 120 in remote locations permits an operating surgeon viewing the surgeon's console to communicate with a surgical assistant viewing an assistant monitor. In addition, a student surgeon at one surgeon console may communicate with a remote proctor at another surgeon console.

In accordance with another embodiment, a remote user or proctor may have controls for movement of a synthetic image, such as a synthetic image 120. The movement of the synthetic image may be watched by a surgeon or student at the surgeon console, permitting the user to learn surgical procedures and motions, and to mimic those motions with the surgeon or student's controls (and thus the tools).

Range of Motion Limits

The linkages for the robotic arm assemblies of the patient side cart have a limited range of movement, limiting the movement of the tools supported by each arm or linkage. When the robot for a patient encounters range of motion limits, it is not always obvious to a surgeon (new or experienced) why the robot is not able to continue moving. In a telesurgical system, there are typically two sources of range of motion limits: joint limits of the master manipulator and joint limits of the slave manipulator.

In accordance with an embodiment, the modeling component 108 generates a signal to indicate that a limit of the range of movement for a tool is approaching. The signal may be used, for example, to generate a visual cue to the surgeon, such as color coding of the part(s) that have reached a limit. Alternatively, the limit may be represented with synthetic geometry as a virtual wall 340 (FIG. 6), which may be shown with the synthetic model 120, or may alternately be superimposed over the field of view. The virtual wall 340 is for the right-most tool 124, and it may be shown as concave, flat, or otherwise shaped to match the curvature of a range of motion. The virtual wall 340 is displayed in a position and direction that is perpendicular to the impeded motion direction of the instrument tip.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system comprising:
   a first robotic arm adapted to support and move a tool;
   a second robotic arm adapted to support and move a camera configured to capture an image of a camera field of view;

an input device;

a display; and a processor configured to:
- display a first synthetic image, the first synthetic image comprising:
  - a first synthetic image of the tool, wherein the first synthetic image of the tool includes a portion of the tool inside of the camera field of view and a portion of the tool outside of the camera field of view; and
  - a synthetic projection of the camera field of view;
- receive a user input at the input device; and
- responsive to the user input, change the display of the first synthetic image to a display of a second synthetic image including a second synthetic image of the tool that is different from the first synthetic image of the tool.

2. The system of claim 1, wherein the second synthetic image of the tool is from a view angle different from a view angle of the camera field of view.

3. The system of claim 1, wherein the second synthetic image of the tool includes a portion of the tool not visible in the first synthetic image of the tool.

4. The system of claim 1, wherein the second synthetic image includes a synthetic image of the first robotic arm.

5. The system of claim 1, wherein the second synthetic image includes a synthetic image of the camera.

6. The system of claim 1, wherein the second synthetic image is displayed in a boundary area around a display of the captured image of the camera field of view.

7. The system of claim 1, wherein the processor is further configured to provide a haptic indication at the input device when changing from the display of the first synthetic image to the display of the second synthetic image.

8. The system of claim 1, wherein the processor is further configured to:
- display the captured image of the camera field of view on the display with the first synthetic image of the tool.

9. The system of claim 8, wherein the first synthetic image is displayed in a first window on the display and the captured image of the camera field of view is displayed in a second window on the display.

10. The system of claim 8, wherein the first synthetic image is displayed in a first window on the display and the captured image of the camera field of view is displayed in a second window on the display, the second window at least partially superimposed over the first window.

11. A method comprising:
- displaying a first synthetic image, the first synthetic image comprising a first synthetic image of a tool, wherein the tool is supported by a first robotic arm and a camera is supported by a second robotic arm, wherein the first synthetic image of the tool includes a portion of the tool inside of a field of view of the camera and a portion of the tool outside of the field of view of the camera, and wherein the first synthetic image further comprises a synthetic projection of the field of view of the camera;
- receiving a user input at an input device configured to move at least one of the first or second robotic arms; and
- responsive to the user input, changing the displaying of the first synthetic image to displaying of a second synthetic image including a second synthetic image of the tool that is different from the first synthetic image of the tool.

12. The method of claim 11, wherein the second synthetic image of the tool is from a view angle different from a view angle of the field of view of the camera.

13. The method of claim 11, wherein the second synthetic image of the tool includes a portion of the tool not visible in the first synthetic image of the tool.

14. The method of claim 11, wherein the second synthetic image includes a synthetic image of the first robotic arm.

15. The method of claim 11, wherein the second synthetic image includes a synthetic image of the camera.

16. The method of claim 11, wherein the second synthetic image is displayed in a boundary area around a display of a captured image of the field of view of the camera.

17. The method of claim 11, further comprising:
- providing a haptic indication at the input device when changing from the displaying of the first synthetic image to the displaying of the second synthetic image.

18. The method of claim 11, further comprising:
- displaying a captured image of the field of view of the camera on a display with the first synthetic image of the tool.

19. The method of claim 18, wherein the first synthetic image is displayed in a first window on a display and the captured image of the field of view of the camera is displayed in a second window on the display.

20. The method of claim 18, wherein the first synthetic image is displayed in a first window on the display and the captured image of the field of view of the camera is displayed in a second window on the display, the second window at least partially superimposed over the first window.

* * * * *